(12) United States Patent
Yoshida et al.

(10) Patent No.: US 11,479,552 B2
(45) Date of Patent: Oct. 25, 2022

(54) SUBSTITUTED PIPERIDINE COMPOUNDS AND THEIR USE

(71) Applicant: Eisai R&D Management Co., Ltd., Tokyo (JP)

(72) Inventors: Yu Yoshida, Tsukuba (JP); Yoichi Kita, Tsukuba (JP); Makoto Kotake, Tsukuba (JP); Keiichi Sorimachi, Tsukuba (JP); Toshiyuki Ohfusa, Nagareyama (JP); Takafumi Motoki, Tsukuba (JP); Taro Asaba, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 17/376,452

(22) Filed: Jul. 15, 2021

(65) Prior Publication Data
US 2022/0017517 A1    Jan. 20, 2022

(30) Foreign Application Priority Data
Jul. 17, 2020  (JP) .............................. JP2020-122864

(51) Int. Cl.
*C07D 401/14*   (2006.01)
*C07D 471/08*   (2006.01)

(52) U.S. Cl.
CPC .................. *C07D 471/08* (2013.01)

(58) Field of Classification Search
CPC .. C07D 401/14; C07D 451/02; A61K 31/506; A61P 25/00; A61P 43/00
USPC .................. 544/332, 330; 514/275
See application file for complete search history.

(56) References Cited

FOREIGN PATENT DOCUMENTS

| | | |
|---|---|---|
| JP | H10-229887 | 9/1998 |
| JP | H10-327888 | 12/1998 |
| JP | H10-327889 | 12/1998 |
| JP | H11-178588 | 7/1999 |
| JP | 2008-517032 | 5/2008 |
| JP | 4765627 | 9/2011 |
| JP | 2016-512536 | 4/2016 |
| WO | WO 1996/034877 | 11/1996 |
| WO | WO 2005/028438 | 3/2005 |
| WO | WO 2006/045716 | 5/2006 |
| WO | WO 2007/139149 | 12/2007 |
| WO | WO 2014/159591 | 10/2014 |

OTHER PUBLICATIONS

Hatanaka et al., "Discovery of a Novel Orally Available Selective Orexin 2 Receptor Agonist, E2086, as a Therapeutic Drug for Narcolepsy and Other Hypersomnia Disorder," Presentation, World Sleep Congress, Mar. 11-16, 2022, Rome, Italy, 9 pages.

Office Action in Pakistani Patent Application No. 537/2021, dated Mar. 22, 2022, 3 pages.
Busquets et al, "Decreased Plasma Levels of Orexin-A in Sleep Apnea," Respiration, 2004, 71:575-579.
Chemelli et al, "Narcolepsy in orexin knockout mice: molecular genetics of sleep regulation," Cell, 1999, 98:437-451.
Fujiki et al, "Specificity of Direct Transition from Wake to REM Sleep in Orexin/ataxin-3 Transgenic Narcoleptic Mice," Author Manuscript, Experimental Neurology, 2009, 217:46-54.

(Continued)

*Primary Examiner* — Charanjit Aulakh
(74) *Attorney, Agent, or Firm* — Fish & Richardson P.C.

(57) ABSTRACT

Provided are compounds represented by the following formulas (I), (II), (III) and (IV) having orexin type 2 receptor-activating activity, or their pharmaceutically acceptable salts.

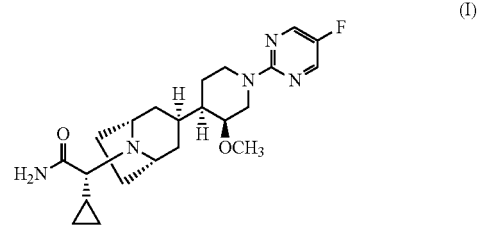

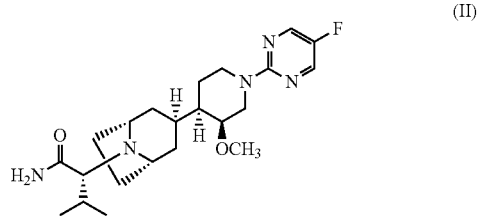

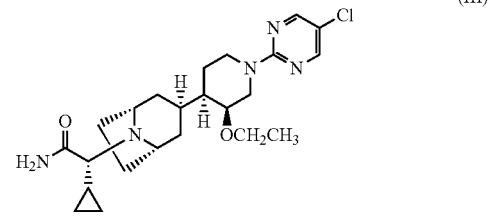

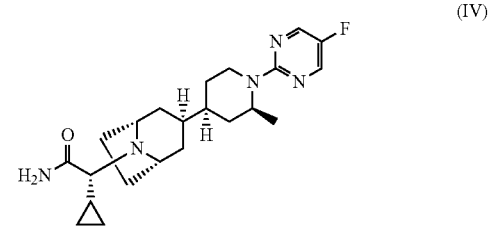

9 Claims, 3 Drawing Sheets

(56) References Cited

OTHER PUBLICATIONS

Hara et al, "Genetic Ablation of Orexin Neurons in Mice Results in Narcolepsy, Hypophagia, and Obesity," Neuron, 2001, 30:345-354.
International Search Report in International Appln. No. PCT/JP2021/026649, dated Aug. 17, 2021, 2 pages.
Lin et al, "The sleep disorder canine narcolepsy is caused by a mutation in the hypocretin (orexin) receptor 2 gene", Cell, 1999, 98:365-376.
Mieda et al, "Orexin (Hypocretin) Receptor Agonists and Antagonists for Treatment of Sleep Disorders—Rationale for Development and Current Status," CNS Drugs, 2013, 27:83-90.
Mieda et al, "Orexin peptides prevent cataplexy and improve wakefulness in an orexin neuron-ablated model of narcolepsy in mice," Proceedings of the National Academy of Sciences, 2004, 101(13):4649-4654.
Sakurai et al., "Orexins and Orexin Receptors: a family of hypothalamic neuropeptides and G protein-coupled receptors that regulate feeding behavior," Cell, 1998, 92:573-585.
Sato et al, "Exploiting Chemical Probes for Identifying Drug Target Proteins," Journal-Mass Spectrometry Society of Japan, 2003, 51(5):492-498 (with English Translation).
Takeda.com [Online], "Takeda Provides Update on TAK-994 Clinical Program," Oct. 5, 2021, [Retrieved on Oct. 12, 2021], retrieved from: URL<https://www.takeda.com/newsroom/newsreleases/2021/takeda-provides-update-on-tak-994-clinical-program/>, 3 pages.
Thannickal et al, "Hypocretin (orexin) cell loss in Pairkinson's disease," Brain, 2007, 130:1586-1595.
Willie et al, "Distinct Narcolepsy Syndromes in Orexin Receptor-2 and Orexin Null Mice: Molecular Genetic Dissection of Non-REM and REM Sleep Regulatoiy Processes," Neuron, 2003, 38:715-730.

SUBSTITUTED PIPERIDINE COMPOUNDS AND THEIR USE

CROSS-REFERENCE TO RELATED APPLICATION

This application claims the benefit of Japanese patent application No. 2020-122864 filed on Jul. 17, 2020, the disclosure of which is herein incorporated by reference in its entirety.

TECHNICAL FIELD

The present invention relates to substituted piperidine compounds having orexin type 2 receptor-activating activity, and to their pharmaceutically acceptable salts and medical use. The invention further relates to drugs comprising the compounds as active ingredients.

BACKGROUND

Orexin-A (OX-A) and orexin-B (OX-B), two types of intracerebral neuropeptides produced specifically by specific neurons localized in the outer field of the cerebral hypothalamus, were discovered as endogenous ligands of orexin receptors (PTLs 1-4), which are G protein-coupled receptors present mainly in the cerebrum (see PTL 5 and NPL 1). Two subtypes of orexin receptors are known, the type 1 subtype $OX_1$ receptors (OX1R) and the type 2 subtype $OX_2$ receptors (OX2R). Orexins have been found to promote rat feeding behavior (NPL 1).

An OX2R gene mutation has been reported to be one cause of canine narcolepsy (NPL 2), and orexin knockout mice exhibit narcolepsy-like symptoms that are highly similar to human or canine narcolepsy (NPL 3). Research using transgenic mice with modified orexin neurons, and double transgenic mice obtained by cross-breeding these mice with orexin-overexpressing transgenic mice, has shown that narcolepsy-like symptoms exhibited by modification of orexin neurons are eliminated by persistent expression of orexin (NPL 4). Similarly, it has been found that intracerebroventricular administration of OX-A to transgenic mice with modified orexin neurons inhibits cataplexy (affective cataplexy)-like stopping action, and improves symptoms of narcolepsy by increasing alertness, for example (NPL 4). Research in OX2R knockout mice also suggests that OX2R is important for maintaining alertness (NPL 5). It has also been suggested that loss of orexin nerves is a cause of daytime sleepiness in Parkinson's disease patients (NPL 6). Furthermore it has been suggested that plasma OX-A concentration levels are low in sleep apnea syndrome patients (NPL 7). On this basis, it was suggested that OX2R agonists can serve as narcolepsy treatments or therapeutic agents for other sleep disorders that exhibit hypersomnia (NPL 8).

It is therefore believed that compounds with OX2R-activating activity can be utilized as therapeutic agents for narcolepsy, idiopathic hypersomnia, hypersomnia, sleep apnea syndrome, states of impaired consciousness such as coma, narcolepsy syndrome accompanied by narcolepsy-like symptoms, and hypersomnia syndrome accompanied by daytime hypersomnia (for example, Parkinson's disease, Guillain-Barré syndrome and Kleine Levin syndrome).

TAK-925, a compound with OX2R-activating activity, has entered phase I trials (Intravenous Infusion) for healthy persons and narcolepsy patients.

CITATION LIST

Patent Literature

[PTL 1] International Patent Publication No. 1996/34877
[PTL 2] Japanese Unexamined Patent Publication HEI No. 10-327888
[PTL 3] Japanese Unexamined Patent Publication HEI No. 10-327889
[PTL 4] Japanese Unexamined Patent Publication HEI No. 11-178588
[PTL 5] Japanese Unexamined Patent Publication HEI No. 10-229887

Non-Patent Literature

[NPL 1] Sakurai T. et al, Cell, 1998, 92, 573-585
[NPL 2] Lin L. et al, Cell, 1999, 98, 365-376
[NPL 3] Chemelli R. M. et al, Cell, 1999, 98, 437-451
[NPL 4] Mieda M. et al, Proc. Natl. Acad. Sci. USA, 2004, 101, 4649-4654
[NPL 5] Willie J. T. et al, Neuron, 2003, 38, 715-730
[NPL 6] Thannickal T. C. et al, Brain. 2007, 130, 1586-1595
[NPL 7] Busquets X. et al, Respiration, 2004, 71, 575-579
[NPL 8] Mieda M. et al, CNS Drugs, 2013, 27, 83-90

SUMMARY

It is an object of the present invention to provide piperidine compounds having orexin type 2 receptor-activating activity, and to their pharmaceutically acceptable salts and to pharmaceutical compositions comprising them.

Specifically, the invention relates to the following <1> to <21>.

<1> A compound selected from the group consisting of (2R)-2-cyclopropyl-2-{(1R,3S,5S)-3-[(3S,4R)-1-(5-fluoropyrimidin-2-yl)-3-methoxypiperidin-4-yl]-8-azabicyclo[3.2.1]octan-8-yl}acetamide represented by the following formula (I):

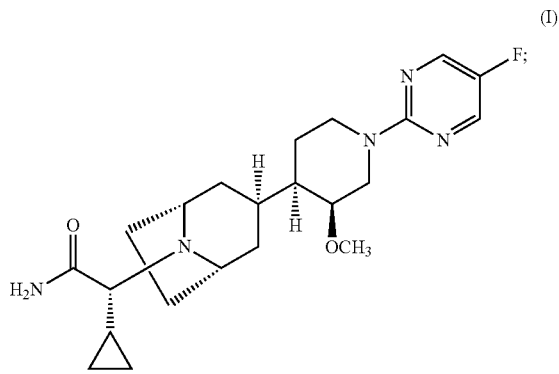 [SMILES: CO[C@@H]1CN(c2ncc(F)cn2)CC[C@@H]1[C@@H]1C[C@H]2CC[C@@H](C1)N2C[C@@H](C(N)=O)C1CC1]

(R)-2-((1R,3S,5S)-3-((3S,4R)-1-(5-fluoropyrimidin-2-yl)-3-methoxypiperidin-4-yl)-8-azabicyclo[3.2.1]octan-8-yl)-3-methylbutaneamide represented by the following formula (II):

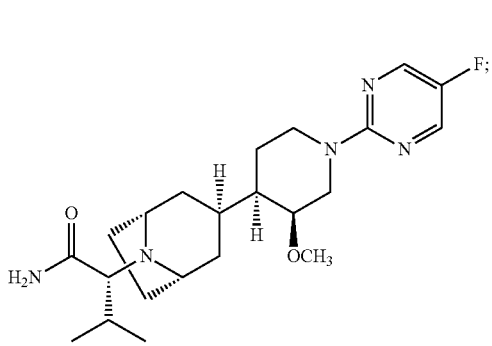

(R)-2-((1R,3S,5S)-3-((3S,4R)-1-(5-chloropyrimidin-2-yl)-3-ethoxypiperidin-4-yl)-8-azabicyclo[3.2.1]octan-8-yl)-2-cyclopropyl acetamide represented by the following formula (III):

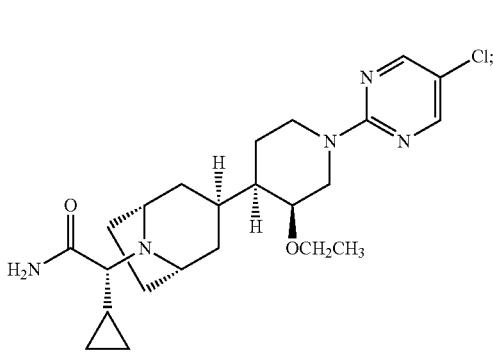

and (R)-2-cyclopropyl-2-((1R,3S,5S)-3-((2S, 4S)-1-(5-fluoropyrimidin-2-yl)-2-methylpiperidin-4-yl)-8-azabicyclo[3.2.1]octan-8-yl)acetamide represented by the following formula (IV):

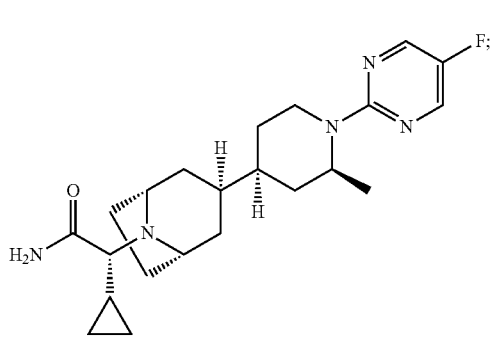

or a pharmaceutically acceptable salt thereof.

<2> (2R)-2-cyclopropyl-2-{(1R,3S,5S)-3-[(3S,4R)-1-(5-fluoropyrimidin-2-yl)-3-methoxypiperidin-4-yl]-8-azabicyclo[3.2.1]octan-8-yl}acetamide represented by the following formula (I):

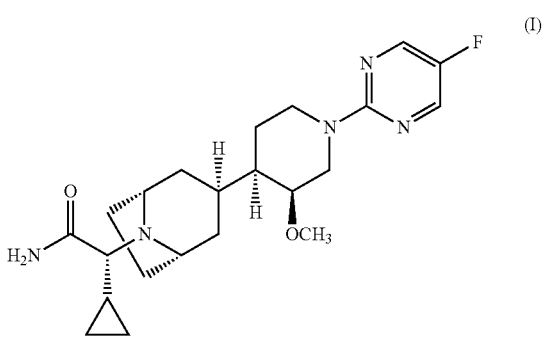 [SMILES: CO[C@@H]1CN(c2ncc(F)cn2)CC[C@@H]1[C@@H]1C[C@H]2CC[C@@H](C1)N2[C@@H](C(N)=O)C1CC1]

or a pharmaceutically acceptable salt thereof.

<3> (R)-2-((1R,3S,5S)-3-((3S,4R)-1-(5-Fluoropyrimidin-2-yl)-3-methoxypiperidin-4-yl)-8-azabicyclo[3.2.1]octan-8-yl)-3-methylbutaneamide represented by the following formula (II):

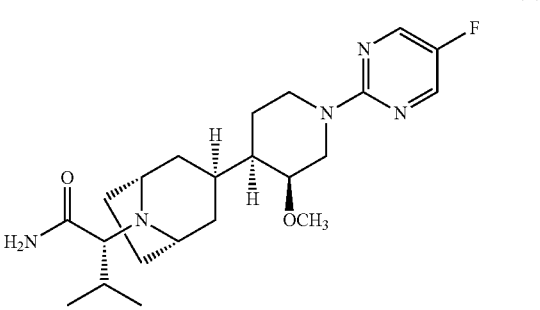

or a pharmaceutically acceptable salt thereof.

<4> (R)-2-((1R,3S,5S)-3-((3S,4R)-1-(5-Chloropyrimidin-2-yl)-3-ethoxypiperidin-4-yl)-8-azabicyclo[3.2.1]octan-8-yl)-2-cyclopropyl acetamide represented by the following formula (III):

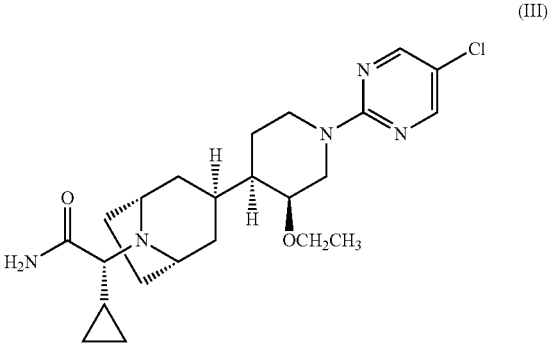 [SMILES: CCO[C@@H]1CN(c2ncc(Cl)cn2)CC[C@@H]1[C@@H]1C[C@H]2CC[C@@H](C1)N2[C@@H](C(N)=O)C1CC1]

or a pharmaceutically acceptable salt thereof.

<5> (R)-2-Cyclopropyl-2-((1R,3S,5S)-3-((2S, 4S)-1-(5-fluoropyrimidin-2-yl)-2-methylpiperidin-4-yl)-8-azabicyclo[3.2.1]octan-8-yl)acetamide represented by the following formula (IV):

(IV)

or a pharmaceutically acceptable salt thereof.

<6> A pharmaceutical composition comprising the compound or a pharmaceutically acceptable salt thereof according to any one of <1> to <5> above.

<7> An orexin type 2 receptor agonist comprising the compound or a pharmaceutically acceptable salt thereof according to any one of <1> to <5> above.

<8> A therapeutic agent for narcolepsy comprising the compound or a pharmaceutically acceptable salt thereof according to any one of <1> to <5> above.

<9> A method of treating narcolepsy, comprising administering to a subject a pharmacologically effective dose of the compound or a pharmaceutically acceptable salt thereof according to any one of <1> to <5> above.

<10> A method of activating orexin type 2 receptor, comprising administering to a subject a pharmacologically effective dose of the compound or a pharmaceutically acceptable salt thereof according to any one of <1> to <5> above.

<11> A method of treating narcolepsy, comprising administering to a subject the compound or a pharmaceutically acceptable salt thereof according to any one of <1> to <5> above.

<12> Use of the compound or a pharmaceutically acceptable salt thereof according to any one of <1> to <5> above for the manufacture of a pharmaceutical composition for the treatment of narcolepsy.

<13> The compound or a pharmaceutically acceptable salt thereof according to any one of <1> to <5> above for use in the treatment of narcolepsy.

<14> A therapeutic agent for cataplexy comprising the compound or a pharmaceutically acceptable salt thereof according to any one of <1> to <5> above.

<15> A method of treating cataplexy, comprising administering to a subject a pharmacologically effective dose of the compound or a pharmaceutically acceptable salt thereof according to any one of <1> to <5> above.

<16> The compound or a pharmaceutically acceptable salt thereof according to any one of <1> to <5> above for use in the treatment of cataplexy.

<17> Use of the compound or a pharmaceutically acceptable salt thereof according to any one of <1> to <5> above for the manufacture of a pharmaceutical composition for the treatment of cataplexy.

<18> A therapeutic agent for hypersomnia syndrome comprising the compound or a pharmaceutically acceptable salt thereof according to any one of <1> to <5> above.

<19> A method of treating hypersomnia syndrome, comprising administering to a subject a pharmacologically effective dose of the compound or a pharmaceutically acceptable salt thereof according to any one of <1> to <5> above.

<20> The compound or a pharmaceutically acceptable salt thereof according to any one of <1> to <5> above for use in the treatment of hypersomnia syndrome.

<21> Use of the compound or a pharmaceutically acceptable salt thereof according to any one of <1> to <5> above for the manufacture of a pharmaceutical composition for the treatment of hypersomnia syndrome.

The substituted piperidine compounds represented by formulas (I), (II), (III) and (IV) (hereunder referred to as compounds (I), (II), (III) and (IV)) or their pharmaceutically acceptable salts according to the invention have orexin type 2 receptor-activating activity as indicated by the activity data in the Pharmacological Test Examples described below. Compounds (I), (II), (III) and (IV) of the invention have orexin type 2 receptor-activating activity and can be used as therapeutic agents for narcolepsy.

DETAILED DESCRIPTION

Figure 1:
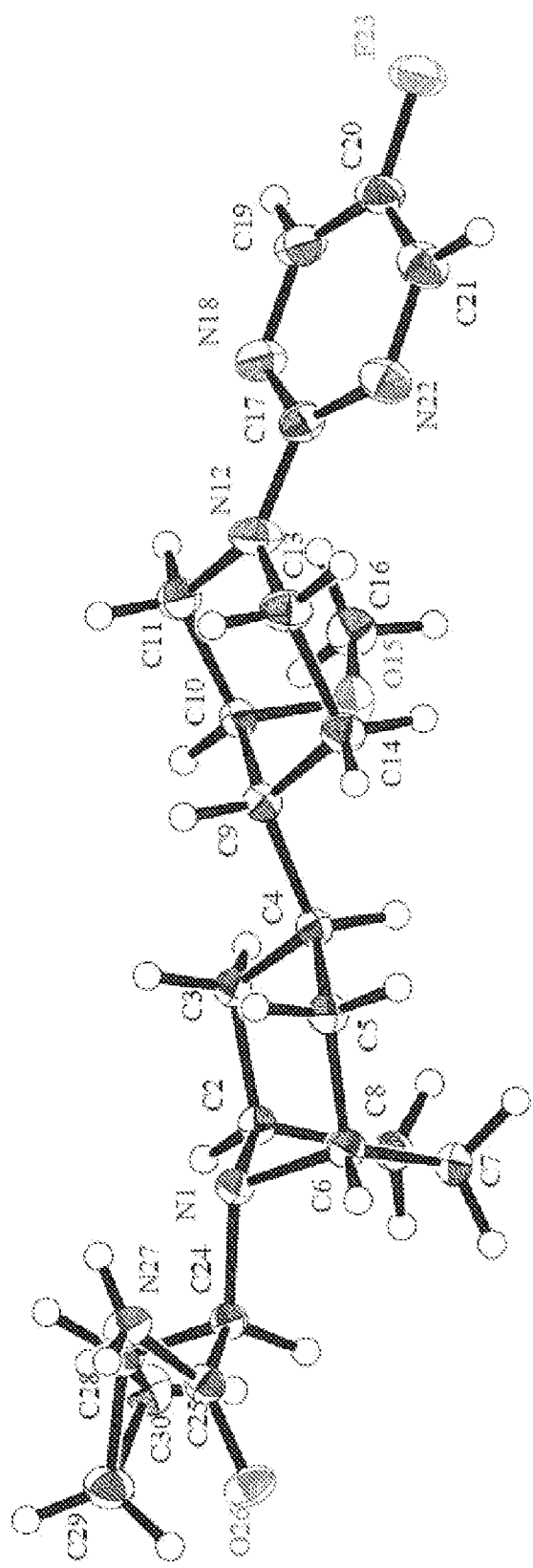
FIG. 1 is an ORTEP diagram showing the results of X-ray crystallographic analysis of the compound obtained in Example 1.

The present invention will now be explained in detail.

Polymorphic crystals of the compounds of the invention may also exist, and any crystal form or mixture thereof as well as amorphous forms, may be used without any restrictions, while the compounds of the invention also include both anhydrous and solvated (especially hydrated) forms.

Isotope-labeled forms of compounds (I), (II), (III) and (IV) are also encompassed by the invention. An isotope-labeled compound is the same as any of compounds (I), (II), (III) and (IV), except that one or more atoms are replaced with an atom having a different atomic mass or mass number than the atomic mass or mass number usually observed in nature. Examples of isotopes that may be incorporated into compounds of the invention include isotopes of hydrogen, carbon, nitrogen, oxygen, fluorine, phosphorus, sulfur, iodine and chlorine, and specifically $^{2}H$, $^{3}H$, $^{11}C$, $^{14}C$, $^{15}N$, $^{18}O$, $^{18}F$, $^{32}P$, $^{35}S$, $^{123}I$ and $^{125}I$.

Isotope-labeled compounds, such as compounds incorporating radioactive isotopes such as $^{3}H$ and/or $^{14}C$, are useful for tissue distribution assays of drugs and/or substrates. The isotopes $^{3}H$ and $^{14}C$ are considered useful because of their ease of preparation and detection. The isotopes $^{11}C$ and $^{18}F$ are considered useful for PET (Positron Emission Tomography), while the isotope $^{125}I$ is considered useful for SPECT (Single Photon Emission Computed Tomography), and therefore all are useful for brain imaging. Substitution of $^{2}H$ and the like with heavier isotopes affords advantages in certain types of treatment, such as a longer in vivo half-life and lower required dosages due to higher metabolic stability, and are therefore considered useful under some circumstances. Such isotope-labeled compounds can be uniformly prepared by the procedures disclosed in the Examples below, with easily usable isotope-labeled reagents in place of non-isotope-labeled reagents.

A "pharmaceutically acceptable salt", as referred to herein, is not particularly restricted so long as it is one that forms with the compound of the invention, and specific examples include acid addition salts such as inorganic acid salts, organic acid salts or acidic amino acid salts.

Unless otherwise specified, the term "pharmaceutically acceptable salt" as used herein refers to one in which the number of molecules of acid with respect to one molecule of the compound is, without being restrictive, preferably about 0.5 to about 2 molecules of acid with respect to one molecule of the compound, or more preferably about 0.5, about 1 or about 2 molecules of acid with respect to one molecule of the compound, for a salt formed in an appropriate proportion.

Preferred examples of inorganic acid salts include hydrochlorides, hydrobromides, sulfates, nitrates and phosphates, and preferred examples of organic acid salts include acetates, succinates, fumarates, maleates, tartrates, citrates, lactates, stearates, benzoates, methanesulfonates, p-toluenesulfonates and benzenesulfonates.

Preferred examples of acidic amino acid salts include aspartic acid salts and glutamic acid salts.

When any of compounds (I), (II), (III) and (IV) of the invention is obtained in free form, it may be converted to an acceptable salt or hydrate of the compound (I), (II), (II) or (IV) by a common method.

When any one of the compounds (I), (II), (III) and (IV) of the invention is obtained as a salt of the compound (I), (II), (III) or (IV) or a hydrate of the compound (I), (II), (III) or (IV), it may be converted to the free form of the compound (I), (II), (III) or (IV) by a common method.

Various isomers (for example, optical isomers, rotational isomers and stereoisomers) obtained for compounds (I), (II), (III) and (IV) of the invention may be purified and isolated using ordinary separation means such as, for example, recrystallization, a diastereomer salt method, enzymatic resolution or chromatography methods (for example, thin-layer chromatography, column chromatography or gas chromatography).

[Formulation]

The pharmaceutical composition of the invention can be produced by mixing a pharmaceutically acceptable additive with a compound selected from among the compound groups (I), (II), (III) and (IV) or its pharmaceutically acceptable salt. The pharmaceutical composition of the invention can be produced by a known method, such as the method described in General Rules for Preparations of the Japanese Pharmacopoeia, 17th Edition.

The pharmaceutical composition of the invention may be appropriately administered to a patient as suitable for the dosage form.

The dosage of any of compounds (I), (II), (III) and (IV) or their pharmaceutically acceptable salts according to the invention may vary depending on the severity of symptoms, age, gender and body weight of the patient, the dosage form or the type of salt, and the specific type of disease, but it will usually be about 30 µg to 10 g, preferably 100 µg to 5 g and even more preferably 100 µg to 1 g for oral administration, and about 30 µg to 1 g, preferably 100 µg to 500 mg and even more preferably 100 µg to 300 mg for administration by injection, per day for an adult, either at once or in divided doses.

The compounds of the invention may also be used as chemical probes to capture target proteins of physiologically active low molecular weight compounds. Specifically, the compounds of the invention can be converted to affinity chromatography or photoaffinity probes by introducing labeling groups or linkers into portions of the compounds other than the structural portions essential for expression of their activity, by the method described in J. Mass Spectrum. Soc. Jpn. Vol. 51, No. 5 2003, p492-498 or WO2007/139149, for example.

The labeling group or linker used in a chemical probe may be a group from among any of the following (1) to (5), for example.

(1) Protein labeling groups including photoaffinity labeling groups (for example, benzoyl, benzophenone, azide, carbonyl azide, diaziridine, enone, diazo and nitro groups) and chemical affinity groups (for example, ketone groups with the alpha carbon atom substituted with a halogen atom, carbamoyl, ester and alkylthio groups, α,β-unsaturated ketones, Michael acceptors such as esters, and oxirane), (2) cleavable linkers such as —S—S—, —O—Si—O—, monosaccharides (such as glucose or galactose) and disaccharides (such as lactose), and oligopeptide linkers that are cleavable by enzyme reaction, (3) fishing tag groups such as biotin, 3-(4,4-difluoro-5,7-dimethyl-4H-3a and 4a-diaza-4-bora-s-indacen-3-yl)propionyl, (4) detectable markers including radiolabeling groups such as $^{125}$I, $^{32}$P, $^{3}$H and $^{14}$C; fluorescent labeling groups such as fluorescein, rhodamine, dansyl, umbelliferone, 7-nitrofurazanyl, 3-(4,4-difluoro-5,7-dimethyl-4H-3a and 4a-diaza-4-bora-s-indacen-3-yl)propionyl groups; chemiluminescent groups such as lumiferin and luminol; and heavy metal ions such as lanthanoid metal ions and radium ion, or (5) groups that bind with solid phase carriers such as glass beads, glass beds, microtiter plates, agarose beads, agarose beds, polystyrene beads, polystyrene beds, nylon beads and nylon beds.

A probe prepared by introducing a labeling group selected from among (1) to (5) above into a compound of the invention by a method described in the literature mentioned above can be used as a chemical probe for identification of labeled proteins that are useful for discovery of new innovative drug development targets.

EXAMPLES

Compounds (I), (II), (III) and (IV) of the invention can be produced by the processes described in the following examples, and the effects of the compounds can be confirmed by the methods described in the test examples. However, these specific examples are merely illustrative and are not intended to restrict the invention in any way, while various modifications may also be implemented such as are within the scope of the invention.

Compounds mentioned with reference to published documents are produced in the manner described in those documents.

The abbreviations used throughout are those commonly known among those skilled in the art. In particular, the following are used.

n-: normal
tert-: tertiary
$^1$H-NMR: Proton Nuclear Magnetic Resonance spectrometry
MS: Mass Spectrometry
HPLC: High-Performance Liquid Chromatography The term "room temperature" used throughout the Examples and Production Examples generally refers to a range of about 10° C. to 35° C. The percentage values are weight percentages, unless otherwise specified.

The chemical shifts in the proton nuclear magnetic resonance spectra are recorded in δ units (ppm) with respect to tetramethylsilane, and the coupling constants are recorded in Hertz (Hz). The patterns are represented as s: singlet, d doublet, t: triplet, q: quartet, m: multiplet, br: broad and brs: broad singlet.

Mass spectrometry was carried out using an Acquity UPLC™ or Acquity UPC²™ by Waters Co.

For chromatography, Silica Ge160 by Merck (70-230 mesh or 230-400 mesh ASTM) or PSQ60B by Fuji Silysia Chemical, Ltd. was used as the silica gel, or a prepacked column {column: Hi-Flash™ Column (Silicagel) by Yamazen, size: S (16×60 mm), M (20×75 mm), L (26×100 mm), 2L (26×150 mm) or 3 L (46×130 mm), or a Biotage™ SNAP Ultra Silica Cartridge by Biotage Co., size: 10 g, 25 g or 50 g} was used. Fractionation by supercritical fluid chromatography (SFC) was carried out using a Prep100q by Waters Co.

As NH silica gel, either CHROMATOREX NH-DM2035 by Fuji Silysia Chemical, Ltd. was used, or a prepacked column {column: Hi-Flash™ Column (Amino) by Yamazen, size: S (16×60 mm), M (20×75 mm), L (26×100 mm), 2L (26×150 mm) or 3L (46×130 mm), or Presep™ (Luer Lock) $NH_2$(HC) by Wako Pure Chemical Industries, Ltd., size: type M (14 g/25 mL), type L (34 g/70 mL), type 2L (50 g/100 mL) or type 3L (110 g/200 mL)}.

The nomenclature for the following compounds is that indicated in "E-Notebook" version 12 or 13 (Perkin-Elmer), except for commonly used reagents.

Production Example 1

Synthesis of 2-bromo-2-cyclopropyl acetamide

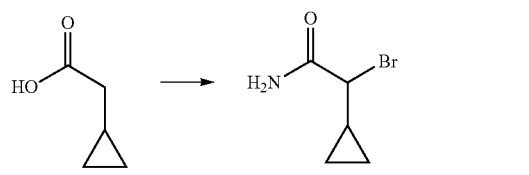 [SMILES: O=C(O)CC1CC1 ; NC(=O)C(Br)C1CC1]

Oxalyl chloride (CAS No. 79-37-8) (3.11 mL, 36.3 mmol) and N,N-dimethylformamide (60.0 μL, 0.775 mmol) were added to a solution of cyclopropylacetic acid (CAS No. 5239-82-7) (3.30 g, 33.0 mmol) in 1,2-dichloroethane (60 mL), and the mixture was stirred for 40 minutes at room temperature. Hydrobromic acid (56.0 mg, 0.330 mmol) and N-bromosuccinimide (CAS No. 128-08-5)(7.04 g, 39.6 mmol) were added to the reaction mixture, which was then heated to reflux for 18 hours. The reaction mixture was added to ammonia (28% aqueous solution, 60 mL, 2.77 mmol) at 0° C., and then ethyl acetate and sodium hydroxide (2 N aqueous solution) were added for separation. The organic layer was dried over anhydrous magnesium sulfate, filtered and concentrated under reduced pressure. The resulting solid was triturated with ethyl acetate/n-heptane and the precipitate was filtered out. The resulting solid was dried under reduced pressure to obtain the title compound (1.20 g).

MS (ESI) m/z: 178[M+H]⁺

Production Example 2

Synthesis of 3-methoxyisonicotinonitrile

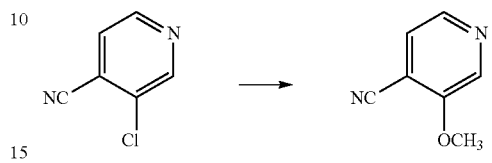

Sodium ethoxide (CAS No. 124-41-4) (3.90 g, 72.2 mmol) was added to a solution of 3-chloro-4-cyanopyridine (CAS No. 68325-15-5) (5.00 g, 36.1 mmol) in tetrahydrofuran (36.0 mL) at room temperature, and the mixture was heated to reflux for 1 hour. Water and ethyl acetate were added to the reaction mixture, and the organic layer was separated off. The organic layer was dried over anhydrous magnesium sulfate, filtered and concentrated under reduced pressure. The resulting solid was triturated with ethyl acetate/n-heptane and the precipitate was filtered out. The resulting solid was dried under reduced pressure to obtain the title compound (1.91 g).

¹H-NMR (400 MHz, CDCl₃) δ (ppm): 4.06 (s, 3H), 7.44 (d, J=5.0 Hz, 1H), 8.37 (d, J=4.5 Hz, 1H), 8.49 (s, 1H).

MS (ESI) m/z: 135[M+H]⁺

Production Example 3

Synthesis of (R)-2-bromo-3-methylbutaneamide

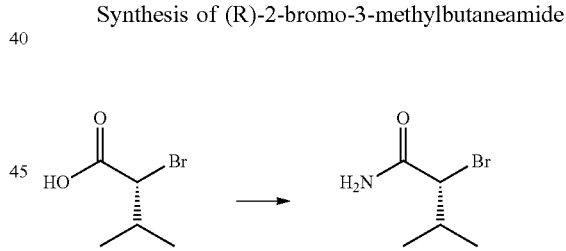

Oxalyl chloride (9.28 mL, 108 mmol) and N,N-dimethylfomamide (30.0 μL, 0.387 mmol) were added to a solution of (R)-2-bromo-3-methylbutyric acid (CAS No. 76792-22-8)(9.80 g, 54.1 mmol) in methylene chloride (100 mL) at 0° C., and the mixture was stirred for 6 hours at room temperature. The reaction mixture was added to ammonia (28% aqueous solution, 50.0 mL, 2.31 mol) at 0° C., and then extracted with methylene chloride. The organic layer was dried over anhydrous magnesium sulfate, filtered and concentrated under reduced pressure. The resulting solid was triturated with ethyl acetate/n-heptane and the precipitate was filtered out. The resulting solid was dried under reduced pressure to obtain the title compound (8.20 g).

¹H-NMR (400 MHz, CDCl₃) δ (ppm): 1.01 (d, J=6.3 Hz, 3H), 1.07 (d, J=6.8 Hz, 3H), 2.34-2.39 (m, 1H), 4.28 (d, J=4.5 Hz, 1H), 5.58 (brs, 1H), 6.41 (brs, 1H).

MS (ESI) m/z: 180[M+H]⁺

Production Example 4

Synthesis of (1R,3s,5S)-3-((3S,4R)-1-(5-fluoropyrimidin-2-yl)-3-methoxypiperidin-4-yl)-8-azabicyclo[3.2.1]octane

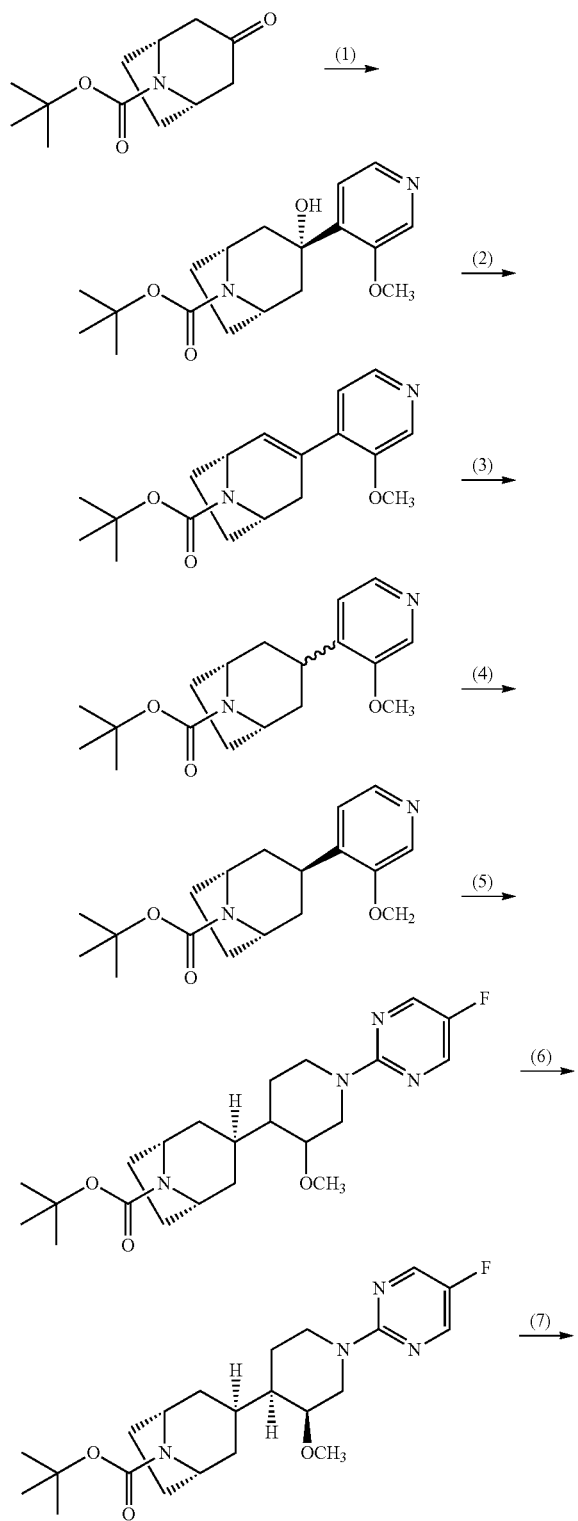

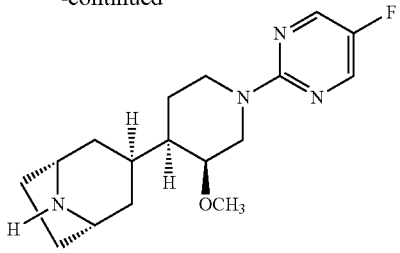

(1) Synthesis of tert-butyl (1R, 3r, 5S)-3-hydroxy-3-(3-methoxypyridin-4-yl)-8-azabicyclo[3.2.1]octane-8-carboxylate After adding 3-methoxyisonicotinonitrile (1.19 g, 8.88 mmol) and bis(pinacolato)diboron (CAS No. 73183-34-3) (2.25 g, 8.88 mmol) to a solution of N-(tert-butoxycarbonyl)-nortropinone (CAS No. 185099-67-6)(1.00 g, 4.44 mmol) in methyl tert-butyl ether (18.0 mL), the mixture was heated to reflux for 16 hours. Sodium carbonate (2 mol/L aqueous solution, 20.0 mL) was added to the reaction mixture at 0° C., and the mixture was stirred for 20 minutes at 0° C. Ethyl acetate was added to the reaction mixture and the organic layer was separated off. The organic layer was dried over anhydrous magnesium sulfate, filtered and concentrated under reduced pressure. The residue was purified by column chromatography (silica gel, 0-20% methanol/ethyl acetate) to obtain the title compound (1.12 g).

$^1$H-NMR (400 MHz, CDCl$_3$) δ (ppm): 1.48 (s, 9H), 1.77 (m, 2H), 1.94-1.99 (m, 2H), 2.21-2.32 (m, 2H), 2.37-2.48 (m, 1H), 2.63-2.74 (m, 1H), 2.78 (s, 1H), 3.96 (s, 3H), 4.22-4.29 (m, 1H), 4.31-4.42 (m, 1H), 7.28 (d, J=5.4 Hz, 1H), 8.22-8.25 (m, 2H).

MS (ESI) m/z: 335[M+H]$^+$

(2) Synthesis of tert-butyl (1R,5S)-3-(3-methoxypyridin-4-yl)-8-azabicyclo[3.2.1]oct-2-ene-8-carboxylate Concentrated sulfuric acid (1.60 mL, 30.0 mmol) was added to tert-butyl (1R, 3r, 5S)-3-hydroxy-3-(3-methoxypyridin-4-yl)-8-azabicyclo[3.2.1]octane-8-carboxylate (610 mg, 1.82 mmol), and the mixture was stirred for 40 minutes at room temperature. The reaction mixture was added to a solution of potassium hydroxide (5.00 g, 89.1 mmol) in water (10.0 mL) at 0° C. Tetrahydrofuran (10.0 mL) and di-tert-butyl dicarbonate (CAS No. 24424-99-5) (478 mg, 2.19 mmol) were added to the reaction mixture, which was then stirred for 10 minutes at room temperature. Ethyl acetate was added to the reaction mixture and the organic layer was separated off. The organic layer was dried over anhydrous magnesium sulfate, filtered and concentrated under reduced pressure. The residue was purified by column chromatography (silica gel, 5-100% ethyl acetate/n-heptane) to obtain the title compound (420 mg).

$^1$H-NMR (400 MHz, CDCl$_3$) δ (ppm): 1.46 (s, 9H), 1.72-1.81 (m, 1H), 1.97-2.03 (m, 2H), 2.05-2.36 (m, 2H), 2.94-3.26 (m, 1H), 3.87 (s, 3H), 4.21-4.61 (m, 2H), 6.30 (brs, 1H), 6.99 (d, J=4.5 Hz, 1H), 8.17 (d, J=5.0 Hz, 1H), 8.21 (s, 1H).

MS (ESI) m/z: 317[M+H]$^+$

(3) Synthesis of tert-butyl (1R,5S)-3-(3-methoxy-pyridin-4-yl)-8-azabicyclo[3.2.1]octane-8-carboxylate After adding 10% palladium-carbon (AD, 52.7% aqueous, 284 mg, 0.126 mmol, product of Kawaken Fine Chemicals Co., Ltd.) to a solution of tert-butyl (1R,5S)-3-(3-methoxypyridin-4-yl)-8-azabicyclo[3.2.1]oct-2-ene-8-carboxylate (400 mg, 1.26 mmol) in methanol (3.00 mL), the mixture was stirred for 1 hour at room temperature under a hydrogen atmosphere. The reaction mixture was filtered with Celite™ and the residue was rinsed with ethyl acetate. The obtained filtrate was concentrated under reduced pressure to obtain a mixture of the endo form and exo form (endo:exo=1:2, 398 mg).

$^1$H-NMR (400 MHz, CDCl$_3$) δ (ppm): 1.49 (s, 6H), 1.50 (s, 3H), 1.61-2.13 (m, 22/3H), 2.40-2.45 (m, 2/3H), 2.96-3.01 (m, 1/3H), 3.47-3.59 (m, 2/3H), 3.88 (s, 1H), 3.90 (s, 2H), 4.16-4.28 (m, 1H), 4.34 (brs, 1H), 7.04 (d, J=4.5 Hz, 2/3H), 7.06 (d, J=5.0 Hz, 1/3H), 8.13-8.23 (m, 2H).

MS (ESI) m/z: 319[M+H]$^+$

(4) Synthesis of tert-butyl (1R,3s,5S)-3-(3-methoxy-pyridin-4-yl)-8-azabicyclo[3.2.1]octane-8-carboxylate Potassium tert-butoxide (281 mg, 2.50 mmol) was added to a solution of tert-butyl (1R,5S)-3-(3-methoxypyridin-4-yl)-8-azabicyclo[3.2.1]octane-8-carboxylate (398 mg, 1.25 mmol) in tert-butanol (4.00 mL), and the mixture was heated to reflux for 17 hours. Ethyl acetate and brine were added to the reaction mixture and the organic layer was separated off. The organic layer was then dried over anhydrous magnesium sulfate, filtered and concentrated under reduced pressure to obtain the title compound (385 mg).

$^1$H-NMR (400 MHz, CDCl$_3$) δ (ppm): 1.49 (s, 9H), 1.58-2.06 (m, 8H), 3.49-3.56 (m, 11H), 3.90 (s, 3H), 4.24 (brs, 1H), 4.34 (brs, 1H), 7.04 (d, J=5.0 Hz, 1H), 8.17-8.19 (m, 2H).

MS (ESI) m/z: 319[M+H]$^+$

(5) Synthesis of tert-butyl (1R,3s,5S)-3-(1-(5-fluoropyrimidin-2-yl)-3-methoxypiperidin-4-yl)-8-azabicyclo[3.2.1]octane-8-carboxylate After adding 10% palladium-carbon (AD, 52.7% aqueous, 7.91 g, 3.52 mmol, product of Kawaken Fine Chemicals Co., Ltd.) to a solution of tert-butyl (1R,3s,5S)-3-(3-methoxypyridin-4-yl)-8-azabicyclo[3.2.1]octane-8-carboxylate (11.2 g, 35.2 mmol) in acetic acid (100 mL), the mixture was stirred for 18 hours at 70° C. under a hydrogen atmosphere. The reaction mixture was filtered with Celite™ and the residue was rinsed with ethylacetate. The filtrate was concentrated under reduced pressure. Ethyl acetate and sodium hydroxide (2 N) were added to the residue, and the organic layer was separated off. The organic layer was dried with ISOLUTE™ HM-N, filtered and concentrated under reduced pressure. After adding N,N-dimethylformamide (50.0 mL), 2-chloro-5-fluoropyrimidine (CAS No. 62802-42-0) (5.21 mL, 42.2 mmol) and potassium carbonate (7.29 g, 52.8 mmol) to the residue, the mixture was stirred for 40 minutes at 80° C. Ethyl acetate and brine were added to the reaction mixture and the organic layer was separated off. The organic layer was dried over anhydrous magnesium sulfate, filtered and concentrated under reduced pressure. The residue was purified by column chromatography (silica gel, 10-60%/ethyl acetate/n-heptane) to obtain the title compound (9.84 g).

$^1$H-NMR (400 MHz, CDCl$_3$) δ (ppm): 1.19-1.30 (m, 3H), 1.46 (s, 9H), 1.46-1.65 (m, 6H), 1.81-1.97 (m, 3H), 2.68 (d, J=14.5 Hz, 1H), 2.71-2.81 (m, 1H), 3.30 (s, 3H), 3.35 (brs, 1H), 4.08-4.31 (m, 2H), 4.64-4.77 (m, 1H), 5.04-5.18 (m, 1H), 8.13 (s, 2H).

MS (ESI) m/z: 421[M+H]$^+$

(6) Synthesis of tert-butyl (1R,3s,5S)-3-(3S,4R)-1-(5-fluoropyrimidin-2-yl)-3-methoxypiperidin-4-yl)-8-azabicyclo[3.2.1]octane-8-carbaoxylate The compound tert-butyl (1R,3s,5S)-3-(1-(5-fluoropyrimidin-2-yl)-3-methoxypiperidin-4-yl)-8-azabicyclo[3.2.1]octane-8-carboxylate (7.00 g, 16.6 mmol) was fractionated 100 mg at a time by supercritical fluid chromatography using CHIRALPAK® IC/SFC (3 cm×25 cm) by Daicel (mobile phase: CO$_2$:methanol (90:10), 120 bar, 40° C., flow rate: 100 mL/min), obtaining the subsequently eluting title compound (3.02 g) at a retention time of 8.45 minutes.

$^1$H-NMR (400 MHz, CDCl$_3$) δ (ppm): 1.17-1.29 (m, 3H), 1.46 (s, 9H), 1.46-1.66 (m, 6H), 1.85-1.97 (m, 3H), 2.68 (d, J=15.0 Hz, 1H), 2.75 (td, J=12.9, 3.2 Hz, 1H), 3.30 (s, 3H), 3.35 (brs, 1H), 4.11-4.31 (m, 2H), 4.66-4.76 (m, 1H), 5.10 (dt J=14.4, 2.6 Hz, 1H), 8.13 (s, 2H).

MS (ESI) m/z: 443[M+Na]$^+$ (Analysis conditions) Supercritical fluid chromatography using CHIRALPAK™ IC-3 (3.0 mm×50 mm) by Daicel (mobile phase: CO$_2$:methanol (85:15), 40° C., flow rate: 1.2 mL/min, detection: UV (254 nm)).

(Analysis results) The retention time of the title compound was 1.34 minutes and the optical purity was >99% ee.

(7) Synthesis of (1R,3s,5S)-3-(3S,4R)-1-(5-fluoropyrimidin-2-yl)-3-methoxypiperidin-4-yl)-8-azabicyclo[3.2.1]octane Trifluoroacetic acid (5.00 mL, 64.9 mmol) was added to tert-butyl (1R,3s,5S)-3-((3S,4R)-1-(5-fluoropyrimidin-2-yl)-3-methoxypiperidin-4-yl)-8-azabicyclo[3.2.1]octane-8-carboxylate (1.00 g, 2.38 mmol), and the mixture was stirred for 20 minutes at room temperature. The reaction mixture was concentrated under reduced pressure. Aqueous saturated 2 N sodium hydroxide was added to the residue and extraction was performed with ethyl acetate (3 times). The combined organic layers were dried over anhydrous magnesium sulfate, filtered and concentrated under reduced pressure to obtain the tide compound (620 mg).

MS (ESI) m/z: 321[M+H]$^+$

Production Example 5

Synthesis of (S)-2-bromo-2-cyclopropyl acetamide

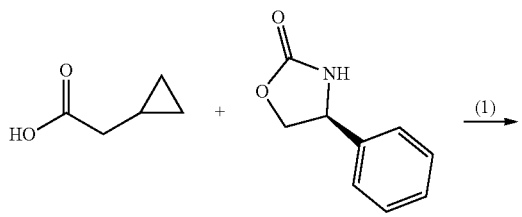

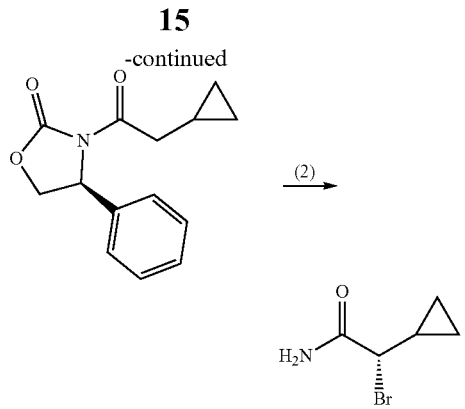

(1) Synthesis of (S)-3-(2-cyclopropylacetyl-4-phenyloxazolidin-2-one

Pivaloyl chloride (302 mL, 2470 mmol) was added to tetrahydrofuran (7000 mL) at room temperature. Cyclopropylacetic acid (238 mL, 2450 mmol) was added at room temperature and the mixture was cooled to 0° C. After dropwise addition of triethylamine (350 mL) over a period of 10 minutes, triethylamine (400 mL, total amount: 5340 mmol) was added and the mixture was stirred for 76 minutes at 0° C. After then adding (S)-4-phenyloxazolidin-2-one (350 g, 2140 mmol) to the reaction mixture all at once, lithium chloride (109 g, 2570 mmol) was further added all at once. The reaction mixture was stirred for 18 hours at room temperature, and then ethyl acetate (7000 mL) and water (3500 mL) were added and the mixture was stirred for 40 minutes at room temperature. The organic layer was separated and rinsed with aqueous 5% sodium hydrogencarbonate (3500 mL) and water (1750 mL), in that order. The obtained organic layer was concentrated to 1750 mL. An azeotropic procedure of adding ethylacetate (2100 mL) and concentrating to 1750 mL was repeated 3 times, after which ethyl acetate (1050 mL) was added and the mixture was concentrated to 1750 mL. The obtained concentrate was stirred, and n-heptane (1000 mL) was added dropwise. The suspension that was produced was stirred for 10 minutes, and n-heptane (2500 mL) was further added dropwise. The liquid mixture was stirred overnight at room temperature, and then further stirred for 3.5 hours at 0° C. The produced solid was filtered using a glass filter and rinsed with ethyl acetate/n-heptane (550 mL of a 1:3 mixture). The resulting solid was dried under reduced pressure to obtain the title compound (407 g).

$^1$H-NMR (400 MHz, CDCl$_3$) δ (ppm): 0.09-0.24 (m, 2H) 0.46-0.58 (m, 2H) 1.00-1.13 (m, 1H), 2.74-2.83 (m, 1H), 2.88-2.98 (m, 1H), 4.25-4.32 (m, 1H), 4.70 (t, J=8.83 Hz, 1H), 5.45 (dd, J=8.83, 3.85 Hz, 1H), 7.28-7.43 (m, 5H).

(2) Synthesis of (S)-2-bromo-2-cyclopropyl acetamide

A 1 M dichloromethane solution of dibutylboron triflate (500 mL, 500 mmol) was added dropwise to a solution of (S)-3-(2-cyclopropylacetyl)-4-phenyloxazolidin-2-one (100 g, 408 mmol) in dichloromethane (1000 mL) over a period of 40 minutes while cooling on ice, and the mixture was stirred for 10 minutes while cooling on ice. After adding N,N-diisopropylethylamine (92 mL, 530 mmol) dropwise over a period of 25 minutes while cooling on ice, the mixture was stirred for 1 hour while cooling on ice. The reaction mixture was then cooled to an internal temperature of −72° C. in a dry ice-ethanol bath. Next, N-bromosuccinimide (80 g, 448 mmol) was added all at once, and the mixture was stirred for 1 hour and 20 minutes in a dry ice-ethanol bath. After adding 28-30% ammonia water (800 mL, 6390 mmol) and tetrahydrofuran (1000 mL), the mixture was stirred for 2 hours in a water bath. The organic layer and aqueous layer were separated, and the aqueous layer was extracted 3 times with ethyl acetate (500 mL). The obtained organic layer was concentrated under reduced pressure, and the obtained residue was purified by silica gel column chromatography (4 kg silica gel, 30-40% ethyl acetate/n-heptane) to obtain 132 g of a crude product. After adding tert-butyl methyl ether (1440 mL) to the obtained crude product and stirring for 1 hour at 50° C. to dissolution, the mixture was further stirred for 1 day at room temperature. The resulting solid was filtered and rinsed with tert-butyl methyl ether (200 mL). The filtrate and rinse solution were combined, ethyl acetate (700 mL) and active carbon (SEISEI SHIRASAGI, 26 g) were added and the mixture was stirred for 30 minutes at room temperature. The active carbon was removed by Celite® filtration, and the active carbon was rinsed with ethyl acetate (700 mL). After combining the filtrate and rinse solution, the mixture was concentrated under reduced pressure to obtain the title compound (97.1 g, 65.9% content).

$^1$H-NMR (400 MHz, CDCl$_3$) δ (ppm): 0.40-0.52 (m, 1H), 0.63-0.73 (m, 1H), 0.77-0.86 (m, 1H), 0.86-0.97 (m, 1H), 1.41-1.50 (m, 1H), 3.59-3.83 (m, 1H), 5.34-5.71 (m, 1H), 5.94-6.30 (m, 1H).

MS (ESI) m/z: 180[M+H]$^+$ (Analysis conditions) Chromatography using CHIRALPAK™ IA (0.46 cm×25 cm×2) by Daicel (mobile phase: ethanol:n-hexane (10:90), 40° C., flow rate: 0.8 mL/min, detection: UV (210 nm)).

(Analysis results) The retention time of the title compound was 24.5 minutes.

Example 1

Synthesis of (R)-2-cyclopropyl-2-((1R,3S,5S)-3-((3S,4R)-1-(5-fluoropyrimidin-2-yl)-3-methoxypiperidin-4-yl)-8-azabicyclo[3.2.1]octan-8-yl)acetamide

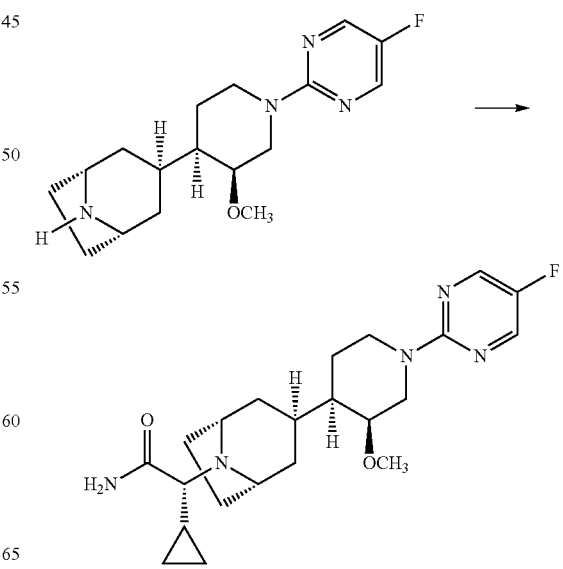

After adding 2-bromo-2-cyclopropyl acetamide (433 mg, 2.43 mmol), cesium carbonate (793 mg, 2.43 mmol) and silver oxide (564 mg, 2.43 mmol) to a solution of (1R,3S,5S)-3-((3S,4R)-1-(5-fluoropyrimidin-2-yl)-3-methoxypiperidin-4-yl)-8-azabicyclo[3.2.1]octane (260 mg, 0.811 mmol) in acetonitrile (4.00 mL), the mixture was stirred for 40 hours at room temperature. The reaction mixture was purified by direct column chromatography (silica gel, 20% methanol/ethyl acetate). The obtained product was dissolved in methanol (10 mL) and supplied onto a Waters Porapak Rxn™ CX (two 2 g cartridges). Each solid phase was rinsed with methanol (20 mL), and then each product was eluted with ammonia (2 mol/L methanol solution, 20 mL) and the eluates were combined and concentrated under reduced pressure. The residue was dissolved in methanol and fractionated by supercritical fluid chromatography using a CHIRALPAK™ (OD-H/SFC (2 cm×25 cm) by Daicel (mobile phase: $CO_2$:methanol (85:15), 120 bar, 40° C., flow rate: 70 mL/min), at 10 mg/500 μL (methanol) per run, obtaining the compound with a retention time of 6.41 minutes (120 mg) as an enantiomeric mixture. The obtained compound was dissolved in methanol and fractionated by supercritical fluid chromatography using a CHIRALPAK™ (IG/SFC (2 cm×25 cm) by Daicel (mobile phase: $CO_2$:methanol (75:25), 120 bar, 40° C., flow rate: 70 mL/min), at 13 mg/500 μL (methanol) per run, obtaining a compound composed mainly of the subsequently eluting component, with a retention time of 9.11 minutes (75 mg). The obtained compound was dissolved in methanol and fractionated by supercritical fluid chromatography using a CHIRALPAK™ (IG/SFC (2 cm×25 cm) by Daicel (mobile phase: $CO_2$:methanol (75:25), 120 bar, 40° C., flow rate: 70 mL/min), at 4 mg/100 μL (methanol) per run, obtaining a compound composed mainly of the subsequently eluting component, with a retention time of 7.52 minutes (52 mg). The obtained compound was dissolved in methanol and fractionated by supercritical fluid chromatography using a CHIRALPAK™ (IG/SFC (2 cm×25 cm) by Daicel (mobile phase: $CO_2$:methanol (75:25), 120 bar, 40° C., flow rate: 70 mL/min), at 7 mg/500 μL (methanol) per run, obtaining the title compound composed mainly of the subsequently eluting component, with a retention time of 7.18 minutes (31.3 mg).

$^1$H-NMR (400 MHz, $CDCl_3$) δ (ppm): 0.28-0.37 (m, 1H), 0.45-0.52 (m, 1H), 0.53-0.58 (m, 1H), 0.60-0.68 (m, 1H), 0.78 (dd, J=8.8, 4.3 Hz, 1H), 1.20-1.27 (m, 2H), 1.32-1.45 (m, 2H), 1.46-1.52 (m, 2H), 1.59-1.65 (m, 3H), 1.70-1.80 (m, 2H), 1.81-1.88 (m, 1H), 2.08 (d, J=9.1 Hz, H), 2.68 (dd, J=14.3, 1.1 Hz, 1H), 2.75 (td, J=12.8, 2.9 Hz, 1H), 3.21-3.24 (m, 1H), 3.30 (s, 3H), 3.36 (brs, 1H), 3.86-3.91 (m, 1H), 4.65-4.76 (m, 1H), 5.10 (dt, J=14.2, 2.4 Hz, 1H),5.14-5.24 (m, 1H), 6.92-7.02 (m, 1H), 8.14 (s, 2H).

MS (ESI) m/z: 418[M+H]$^+$ (Analysis conditions) Chromatography using CHIRALPAK™ IA (0.46 cm×15 cm) by Daicel (mobile phase: ethanol:hexane (20:80), 40° C., flow rate: 1 mL/min, detection: UV (254 nm)).

(Analysis results) The retention time of the title compound was 4.91 minutes and the optical purity was >99% ee.

Preparation of (R)-2-cyclopropyl-2-((1R,3S,5S)-3-((3S,4R)-1-(5-fluoropyrimidin-2-yl)-3-methoxypiperidin-4-yl)-8-azabicyclo[3.2.1]octan-8-yl)acetamide Single Crystal and X-Ray Crystallographic Analysis The title compound obtained in Example 1 (2.97 mg) was dissolved in methanol (1 mL). After placing 500 μL of the solution in a vial, the cap was gently closed (solvent evaporation method). After 1 day, a single crystal of the title compound was obtained in the vial. The obtained single crystal was subjected to X-ray crystallographic analysis under the following conditions. The X-ray crystal structure of the tide compound is shown in FIG. 1.

Analytical instrument: XtaLAB PRO P200 MM007HF (Rigaku, Japan)

Software: CrysAlisPro (Rigaku Oxford Diffraction)

X-rays: Multi-layer mirror monochromated Cu-Kα (40 kV/30 mA)

Measurement: ω axis oscillation method

Camera length: 35 mm

Measuring temperature: −170° C.

The IUPAC name of (R)-2-cyclopropyl-2-((1R,3S,5S)-3-((3S,4R)-1-(5-fluoropyrimidin-2-yl)-3-methoxypiperidin-4-yl)-8-azabicyclo[3.2.1]octan-8-yl)acetamide synthesized in Example 1 is (2R)-2-cyclopropyl-2-{(1R,3S,5S)-3-[(3S,4R)-1-(5-fluoropyrimidin-2-yl)-3-methoxypiperidin-4-yl]-8-azabicyclo[3.2.1]octan-8-yl}acetamide.

Example 2

Synthesis of (R)-2-((1R,3S,5S)-3-((3S,4R)-1-(5-fluoropyrimidin-2-yl)-3-methoxypiperidin-4-yl)-8-azabicyclo[3.2.1]octan-8-yl)-3-methylbutaneamide

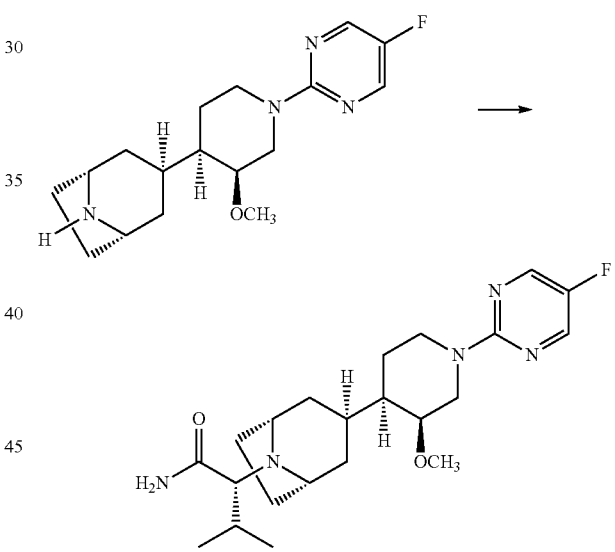

After adding (R)-2-bromo-3-methyl butanamide (326 mg, 1.81 mmol), cesium carbonate (590 mg, 1.81 mmol) and silver oxide (419 mg, 1.81 mmol) to a solution of (1R,3s,5S)-3-((3S,4R)-1-(5-fluoropyrimidin-2-yl)-3-methoxypiperidin-4-yl)-8-azabicyclo[3.2.1]octane (290 mg, 0.905 mmol) in acetonitrile (8.00 mL), the mixture was stirred for 40 hours at room temperature. The reaction mixture was filtered with silica gel and the residue was rinsed with 20% methanol/ethyl acetate. The filtrate was concentrated under reduced pressure. The residue was dissolved in methanol (5 mL) and supplied onto a Waters Porapak Rxn™ CX (bulk, 4 g). The solid phase was rinsed with methanol (40 mL), and then the product was eluted with ammonia (2 N methanol solution, 40 mL) and the eluate was concentrated under reduced pressure. The residue was fractionated by supercritical fluid chromatography using a CHIRALPAK™ (IG/SFC (2 cm×25 cm) by Daicel (mobile phase: $CO_2$:methanol (80:20), 120 bar, 40° C., flow rate: 70 mL/min), at 5 mg per un, obtaining the title compound with a retention time of 4.41 minutes (154 mg). $^1$H-NMR (400 MHz, CDCl$_3$) δ (ppm): 0.95 (d, J=6.8 Hz, 3H), 1.02 (d, J=6.8 Hz, 3H), 1.15-1.56 (m, 8H), 1.75 (td, J=10.8, 6.1 Hz, 3H), 1.86-2.10 (m, 2H), 2.67 (d, J=13.1 Hz, 1H), 2.75 (td, J=12.9, 3.2 Hz, 1H), 2.95 (d, J=4.1 Hz, 1H), 3.19-3.27 (m, 1H), 3.30 (s, 3H), 3.33-3.46 (m, 2H), 4.70 (dt, J=13.3, 2.2 Hz, 1H), 5.06-5.16 (m, 1H), 5.30-5.36 (m, 1H), 6.79 (brd, J=5.0 Hz, 1H), 8.14 (s, 2H).

MS (ESI) m/z: 421[M+H]$^+$

Example 3

Synthesis of (R)-2-((1R,3S,5S)-3-((3S,4R)-1-(5-chloropyrimidin-2-yl)-3-ethoxypiperidin-4-yl)-8-azabicyclo[3.2.1]octan-8-yl)-2-cyclopropyl acetamide

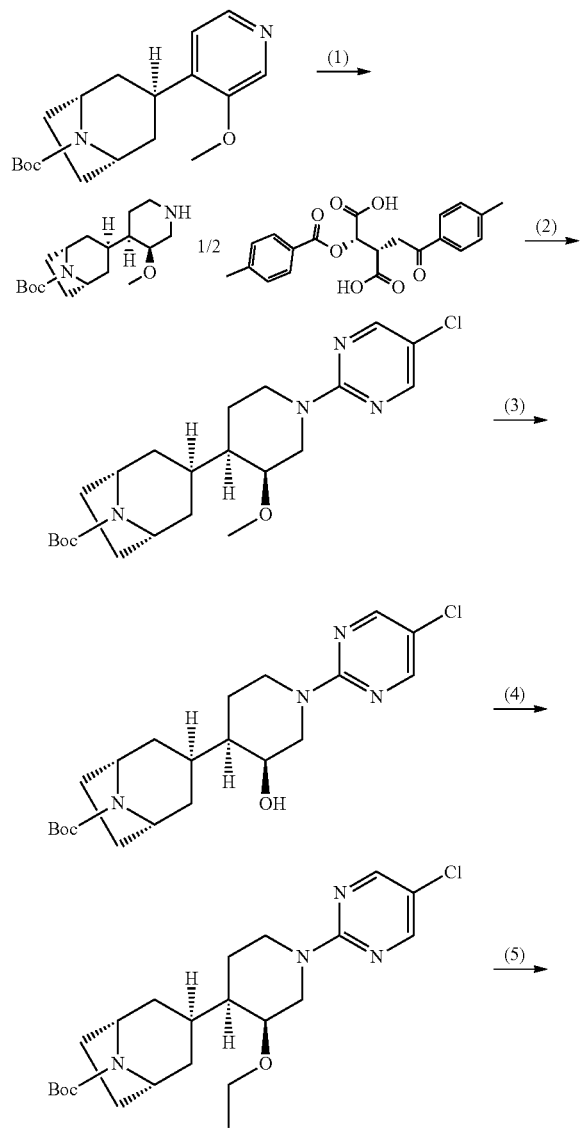

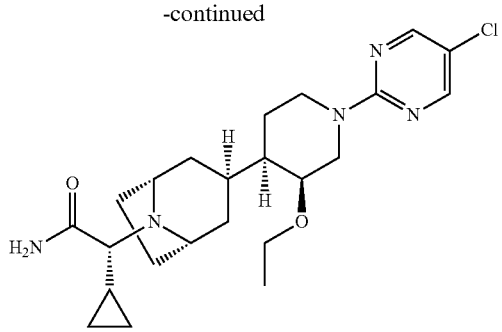

(1) Synthesis of tert-butyl (1R,3s,5S)-3-((3S,4R)-3-methoxypiperidin-4-yl)-8-azabicyclo[3.2.1]octane-8-carboxylate hemi(2S, 3S)-2,3-bis((4-methylbenzoyl)oxy)succinate An acetic acid (160 mL)mixture of tert-butyl(1R,3s,5S)-3-(3-methoxypyridin-4-yl)-8-azabicyclo[3.2.1]octane-8-carboxylate (20 g, 62.8 mmol) and 10% palladium-carbon (type AD, approximately 50% aqueous, 6 g, product of Kawaken Fine Chemicals Co., Ltd.) was stirred overnight at 70° C. under a hydrogen atmosphere. The palladium-carbon was removed by filtration and rinsed with methanol (10-fold volume), and the filtrate was concentrated approximately 2-fold. After adding isopropyl acetate (15-fold volume) and n-heptane (3-fold volume) to the obtained concentrate, the mixture was rinsed with 48% aqueous sodium hydroxide (54.7 mL). After then adding n-heptane (100 mL) and rising with water (5-fold volume), it was concentrated approximately 5-fold. An azeotropic procedure of adding isopropyl acetate (5-fold volume) to the obtained concentrate and concentrating about 5-fold was repeated twice to obtain ten-butyl (1R,3s,5S)-3-(3-methoxypiperidin-4-yl)-8-azabicyclo[3.2.1]octane-8-carboxylate (15.1 g) as an isopropyl acetate solution. After adding (−)-di-para-toluoyl-L-tartaric acid (2.70 g, 6.98 mmol) to a solution of the obtained tert-butyl (1R,3s,5S)-3-(3-methoxypiperidin-4-yl)-8-azabicyclo[3.2.1]octane-8-carboxylate (7.55 g, 23.3 mmol) and (+)-dipivaloyl-D-tartaric acid (1.85 g, 5.82 mmol) in isopropyl acetate (151 mL), acetonitrile (30.2 mL) and methanol (38 mL), the mixture was stirred for 3 days at room temperature to obtain a solid.

The obtained solid was filtered and then rinsed with a mixed solution of isopropyl acetate and acetonitrile (9/1). The obtained mother liquor was concentrated 10-fold, and isopropyl acetate (10-fold volume), aqueous 5 N sodium hydroxide (4.65 ml, 23.269 mmol) and water (4-fold volume) were added. After removing the aqueous layer, it was rinsed with water (4-fold volume). After then concentrating approximately 5-fold, isopropyl acetate (10-fold volume) was added and azeotropic distillation was carried out to about 5-fold, (+)-di-para-toluoyl-D-tartaric acid (3.15 g, 8.144 mmol was added to a solution of (+)-dipivaloyl-D-tartaric acid (1.852 g, 5.817 mmol) in methanol (38 mL), acetonitrile (30.2 mL) and isopropyl acetate (151 mL), and the mixture was stirred overnight at room temperature. The compounds (+)-di-para-toluoyl-D-tartaric acid (0.05 equivalent) and isopropyl acetate (10-fold volume) were then added. The total amount was recovered by concentration, sodium hydroxide neutralization and purified water rinsing, then (+)-di-para-toluoyl-D-tartaric acid (3.15 g, 8.144 mmol) was added to a solution of (+)-dipivaloyl-D-tartaric acid (0.2 equivalent) in isopropyl acetate (151 mL), acetonitrile (30.2 mL) and methanol (38 mL), and the mixture was stirred overnight at room temperature. The compound (+)-di-para-toluoyl-D-tartaric acid (0.05 equivalent) was added to the reaction mixture, and the mixture was stirred for 4 hours at room temperature. The compounds (+)-di-para-toluoyl-D-tartaric acid (0.025 equivalent) and isopropyl acetate (10-fold volume) were as added to the reaction mixture, and the mixture was stirred overnight at room temperature. The total amount was recovered by concentration, sodium hydroxide neutralization and purified water rinsing, (+)-di-para-toluoyl-D-tartaric acid (3.15 g, 8.14 mmol) was added to a solution of (+)-dipivaloyl-D-tartaric acid (0.2 equivalent) in isopropyl acetate (151 mL), acetonitrile (30.2 mL) and methanol (38 mL), and the mixture was stirred overnight at room temperature. Isopropyl acetate (10-fold volume) was then added. After 7 hours, the solid that was produced was filtered and rinsed with isopropyl acetate to obtain the title compound (3.45 g).

(Analysis conditions) Chromatography using CHIRALPAK™ IA (0.46 cm×25 cm) by Daicel (mobile phase: ethanol:n-hexane (20:80),40° C., flow rate: 1.0 mL/min, detection: UV (254 nm)).

(Analysis results) The retention time of the title compound was 8.52 minutes and the optical purity was 99.2% ee.

(2) Synthesis of tert-butyl (1R,3s,5S)-3-((3S,4R)-1-(5-chloropyrimidin-2-yl)-3-methoxypiperidin-4-yl)-8-azabicyclo[3.2.1]octane-8-carboxylate N,N-dimethylformamide (10 mL) containing 2,5-dichloropyrimidine (288 mg, 1.93 mmol), tert-butyl (1R,3s,5S)-3-((3S,4R)-3-methoxypiperidin-4-yl)-8-azabicyclo[3.2.1]octane-8-carboxylate hemi(2S, 3S)-2,3-bis((4-methylbenzoyl)oxy)succinate (500 mg, 0.966 mmol) and potassium carbonate (267 mg, 1.93 mmol) was stirred for 24 hours at 80° C. The reaction mixture was cooled to room temperature, and then water was added and extraction was performed 3 times with ethyl acetate. The organic layer was collected and concentrated. The obtained residue was purified by column chromatography (silica gel, 10-100% ethyl acetate/n-heptane) to obtain the title compound (368 mg).

$^1$H-NMR (400 MHz, CDCl$_3$) δ (ppm): 1.24-1.27 (m, 2H), 1.41-1.49 (m, 2H), 1.46 (s, 9H), 1.61 (brs, 4H), 1.82-1.98 (m, 4H), 2.68 (d, J=14.04 Hz, 1H), 2.75 (td, J=12.91, 3.17 Hz, 1H), 3.30 (s, 3H), 3.36 (brs, 1H), 4.11-4.32 (m, 2H), 4.68-4.80 (m, 1H), 5.12 (dt, J=14.27, 2.61 Hz, 1H), 8.16 (s, 2H).

(3) Synthesis of tert-butyl (1R,3s,5S)-3-((3S,4R)-1-(5-chloropyrimidin-2-yl)-3-hydroxypiperidin-4-yl)-8-azabicyclo[3.2.1]octane-8-carboxylate A mixture of tert-butyl (1R,3s,5S)-3-((3S,4R)-1-(5-chloropyrimidin-2-yl)-3-methoxypiperidin-4-yl)-8-azabicyclo[3.2.1]octane-8-carboxylate (300 ng, 0.687 mmol) and 48% hydrobromic acid (5 mL) was stirred for 20 minutes at room temperature, and then heated for 2.5 hours at 100° C. It was then stirred overnight at room temperature and the obtained reaction mixture was concentrated under reduced pressure. Tetrahydrofuran (10 mL) and aqueous saturated sodium hydrogencarbonate were added to the obtained residue, and then di-tert-butyl dicarbonate (165 mg, 0.755 mmol) was added at room temperature. After confirming completion of the reaction by UPLC, ethyl acetate and water were added and the organic layer was separated. The aqueous layer was again extracted with ethyl acetate and combined with the previously obtained organic layer and dried over anhydrous sodium sulfate, and then concentrated under reduced pressure. The obtained residue was rinsed with a 10%/ethyl acetate/n-heptane mixed solvent to obtain the title compound (226 mg).

$^1$H-NMR (400 MHz, CDCl$_3$) δ (ppm): 1.28-1.34 (m, 2H), 1.46 (s, 9H), 1.59-1.72 (m, 6H), 1.75-1.97 (m, 4H), 2.70-2.83 (m, 1H), 2.91 (dd, J=14.04, 0.91 Hz, 1H), 3.97-4.03 (m, 1H), 4.09-4.34 (m, 2H), 4.68-4.79 (m, 1H), 4.81-4.91 (m, 1H), 8.18 (s, 2H).MS (ESI) m/z: 423[M+H]$^+$ (4) Synthesis of tert-butyl (1R,3s,5S)-3 (3S,4R)-1-(5-chloropyrimidin-2-yl)-3-ethoxypiperidin-4-yl)-8-azabicyclo[3.2.1]octane-8-carboxylate Sodium hydride (60%, dispersed in liquid paraffin, 7.09 mg, 0.177 mmol) was added to a solution of tert-butyl (1R,3s,5S)-3-((3S,4R)-1-(5-chloropyrimidin-2-yl)-3-hydroxypiperidin-4-yl)-8-azabicyclo[3.2.1]octane-8-carboxylate (50 mg, 0.118 mmol) in N,N-dimethylformamide (1 mL), while cooling on ice. After stirring for 30 minutes, ethyl iodide (0.019 mL, 0.236 mmol) was added and the mixture was stirred for 16 hours at room temperature. After adding water and ethyl acetate to the reaction mixture, the organic layer was separated off and concentrated. The obtained residue was purified by column chromatography (silica gel, 1-20% ethyl acetate/n-heptane) to obtain the title compound (42.5 ng).

MS (ESI) m/z: 451[M+H]$^+$ (5) Synthesis of (R)-2-((1R,3S,5S)-3-((3S,4R)-1-(5-chloropyrimidin-2-yl)-3-ethoxypiperidin-4-yl)-8-azabicyclo[3.2.1]octan-8 yl)-2-cyclopropyl acetamide After treating tert-butyl (1R,3s,5S)-3-((3S,4R)-1-(5-chloropyrimidin-2-yl)-3-ethoxypiperidin-4-yl)-8-azabicyclo [3.2.1]octane-8-carboxylate (42.5 mg, 0.094 mmol) with trifluoroacetic acid (1 mL) for 30 minutes, the mixture was concentrated. The obtained residue was dissolved in methanol and supplied onto a Waters Porapak Rxn™ CX (0.4 g). The solid phase was rinsed with methanol (6 mL), and then the product was eluted with ammonia (2 mol/L methanol solution, 6 mL) and the eluate was concentrated under reduced pressure. A mixture of the obtained residue, (S)-2-bromo-2-cyclopropyl acetamide (51.6 mg, 0.188 mmol) obtained by the same procedure as in Production Example 5, potassium carbonate (26.0 mg, 0.188 mmol) and acetonitrile (2 mL) was stirred for 17 days at room temperature. The reaction mixture was filtered using acetonitrile (3 mL) and the obtained filtrate was fractionated by supercritical fluid chromatography using a CHIRALPAK® (IA/SFC (3 cm×25 cm) by Daicel (mobile phase: CO$_2$:methanol (75:25), 120 bar, 40° C., flow rate: 100 mL/min), at 500 μL per run, obtaining the tide compound with a retention time of 7.55 minutes (22.2 mg).

$^1$H-NMR (400 MHz, CDCl$_3$) δ (ppm): 0.26-0.38 (m, 1H), 0.40-0.58 (m, 2H), 0.59-0.68 (m, 1H), 0.71-0.83 (m, 1H), 0.98-1.92 (m, 12H), 1.04 (t, J=7.02 Hz, 3H), 2.07 (brd, J=9.06 Hz, 1H), 2.61-2.81 (m, 2H), 3.13-3.30 (m, 2H), 3.45 (brs, 1H), 3.61-3.75 (m, 1H), 3.84-3.92 (m, 1H), 4.66-4.76 (m, 1H), 4.93-5.11 (m, 1H), 5.17-5.32 (m, 1H), 6.90-7.03 (m, 1H), 8.16 (s, 2H).

MS (ESI) m/z: 448[M+H]$^+$ (Analysis conditions) Supercritical fluid chromatography using CHIRALPAK™ IA-3 (0.46 cm×25 cm) by Daicel (mobile phase: $CO_2$:methanol (80:20), 40° C., flow rate: 1.2 mL/min, detection: UV (257 nm)).

(Analysis results) The retention time of the title compound was 2.19 minutes and the optical purity was >99.9% ee.

Figure 2:
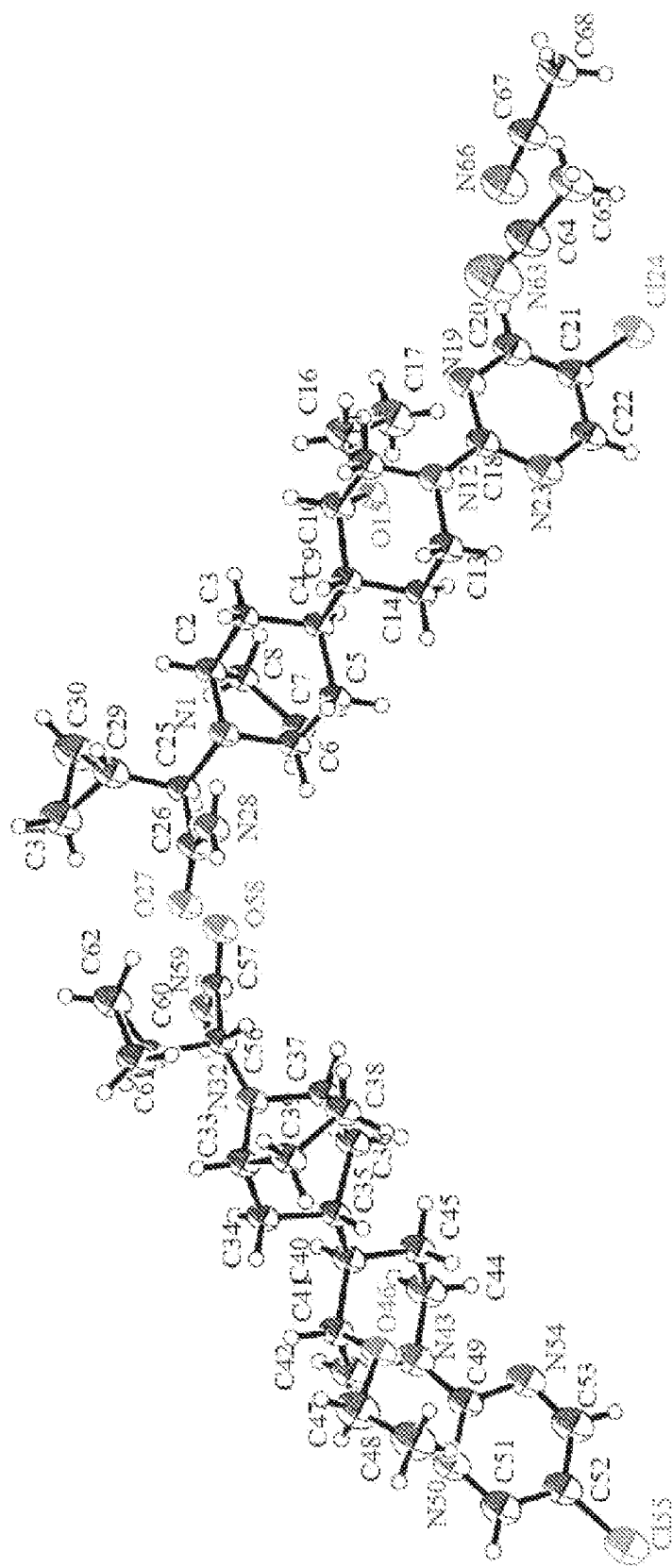
FIG. 2 is an ORTEP diagram showing the results of X-ray crystallographic analysis of the compound obtained in Example 3 (a dimer comprising two added acetonitrile molecules).

Preparation of (R)-2-((1R,3S,5S)-3-((3S,4R)-1-(5-chloropyrimidin-2-yl)-3-ethoxypiperidin-4-yl)-8-azabicyclo[3.2.1]octan-8-yl)-2-cyclopropyl acetamide Single Crystal and X-Ray Crystallographic Analysis The title compound obtained in Example 3 (1.37 mg) was dissolved in acetonitrile (600 μL). After placing 200 μL of the solution in a vial, the cap was gently closed (solvent evaporation method). After 1 day, a single crystal of the title compound (crystal of a dimer with two acetonitrile groups added) was obtained in the vial. The obtained single crystal was subjected to X-ray crystallographic analysis under the following conditions. The X-ray crystal structure of the title compound is shown in FIG. 2.

Analytical instrument: XtaLAB PRO P200 MM007HF (Rigaku, Japan)

Software: CrysAlisPro (Rigaku Oxford Diffraction)

X-rays: Multi-layer mirror monochromated Cu-Kα (40 kV/30 mA)

Measurement: ω axis oscillation method

Camera length: 35 mm

Measuring temperature: −170° C.

Example 4

Synthesis of (R)-2-cyclopropyl-2-((1R,3S,5S)-3-((2S, 4S)-1-(5-fluoropyrimidin-2-yl)-2-methylpiperidin-4-yl)-8-azabicyclo[3.2.1]octan-8-yl)acetamide

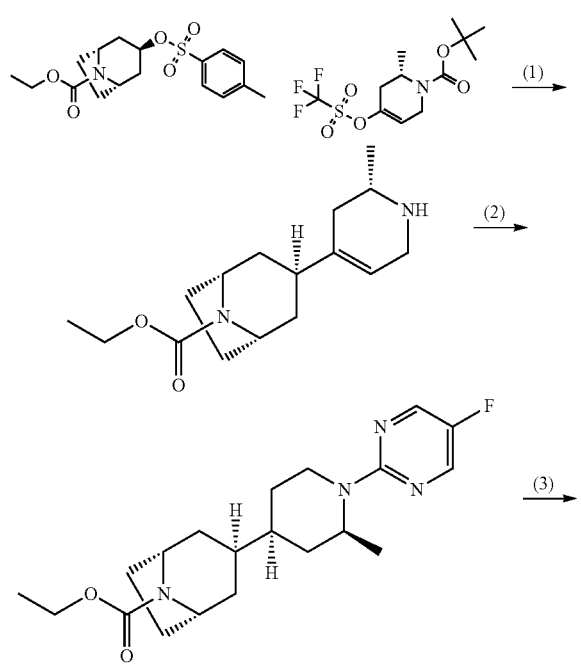

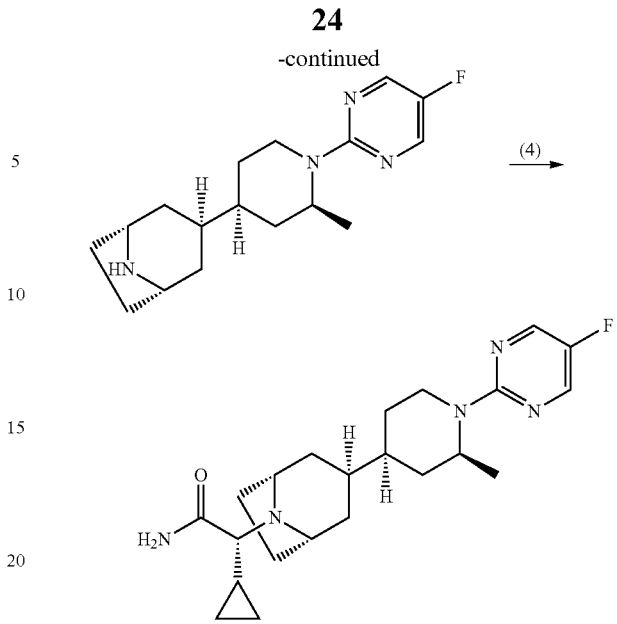

(1) Synthesis of ethyl (1R,3s,5S)-3-((S)-2-methyl-1,2,3,6-tetrahydropyridin-4-yl)-8-azabicyclo[3.2.1]octane-8-carboxylate In a 13 mm screw cap test tube there were added ethyl (1R,3s,5S)-3-(tosyloxy)-8-azabicyclo[3.2.1]octane-8-carboxylate (CAS No. 2236076-85-8) (200 mg, 0.566 mmol), nickel(II) bromide-ethyleneglycol dimethyl ether complex (17.5 mg, 0.057 mmol), 4,4-di-tert-butyl-2,2-dipyridyl (15.2 mg, 0.057 mmol), potassium iodide (94.0 mg, 0.566 mmol) and manganese (62.2 mg, 1.13 mmol). Next, a solution of tert-butyl (S)-2-methyl-4-(((trifluoromethyl)sulfonyl)oxy)-3,6-dihydropyridine-1 (2H)-carboxylate (CAS No. 876922-74-6) (195 mg, 0.566 mmol) in N,N-dimethyl acetamide (4.0 mL) and 4-ethylpyridine (0.064 mL, 0.566 mmol) were added under a nitrogen stream. The obtained mixture was stirred for 12.5 hours at 80° C. under a nitrogen atmosphere. The reaction mixture was cooled to room temperature and then diluted with ethyl acetate. The insolubles were removed by cotton plug filtration and the eluate was distributed with water and ethyl acetate. The aqueous layer was separated off and extracted with ethyl acetate. The organic layers were combined, rinsed 3 times with water and concentrated under reduced pressure, and the coupling reaction product was obtained as a crude product.

Trifluoroacetic acid (1.0 mL) was added to a solution of the obtained crude product in dichloromethane (4.0 mL), and the mixture was stirred for 1 hour at room temperature. Nitrogen was blown into the reaction mixture to distill off the solvent, and the residue was diluted with methanol. The obtained methanol solution was supplied onto a Waters PoraPak Rxn™ CX (20 cc (2 g) cartridge). After rinsing the solid phase with methanol (20.0 mL), it was eluted with ammonia (2 N methanol solution, 20 mL). The eluate was concentrated under reduced pressure to obtain a crude product of the title compound (120 mg).

MS (ESI) m/z: 279[M+H]$^+$ (2) Synthesis of ethyl (1R,3s,5S)-3-((2S,4S)-1-(5-fluoropyrimidin-2-yl)-2-methylpiperidin-4-yl)-8-azabicyclo[3.2.1]octane-8-carboxylate A mixture of ethyl (1R,3s,5S)-3-((S)-2-methyl-1,2,3,6-tetrahydropyridin-4-yl)-8-azabicyclo[3.2.1]octane-8-carboxylate (120 mg, 0.431 mmol), 10% palladium-carbon (48.47% aqueous product, 183 mg, 0.083 mmol, product of N.E. Chemcat Corp.) and methanol (4.0 mL) was stirred for 6.5 hours under a hydrogen atmosphere. The insolubles were removed by Celite™ filtration and concentrated under reduced pressure to obtain the reduced form (113 mg) as a cis/trans mixture.

MS (ESI) m/z: 281[M+H]$^+$

A mixture of the obtained reduced form (113 mg), 2-chloro-5-fluoropyrimidine (0.048 mL, 0.517 mmol), cesium carbonate (281 mg, 0.862 mmol) and N,N-dimethyl acetamide (2.0 mL) was stirred for 8 hours at 100° C. The mixture was purified by column chromatography (silicagel, 0% to 30% ethyl acetate/n-heptane) to obtain the title compound (82.0 mg) as a cis/trans mixture.

MS (ESI) m/z: 377[M+H]$^+$ (Analysis conditions) Supercritical fluid chromatography using CHIRALPAK™ IF-3 (3.0 mm×50 mm) by Daicel (mobile phase: $CO_2$:methanol (70:30), 40° C., flow rate: 1.2 mL/min, detection: UV (210-400 nm)).

(Analysis results) The retention time of the title compound was 1.02 minutes, and the retention time of the trans-form was 1.23 minutes. The cis:trans ratio was 4:5 (peak area ratio), and the optical purity was >99% ee.

The obtained cis/trans mixture was fractionated by supercritical fluid chromatography using a CHIRALPAK® (IF/SFC (3 cm×25 cm) by Daicel (mobile phase: $CO_2$:methanol (70:30), 120 bar, 40° C., flow rate: 100 mL/min), at 10 mg per un, obtaining the first eluting title compound with a retention time of 5.55 minutes (34.0 mg).

$^1$H-NMR (400 MHz, CDCl$_3$) δ (ppm): 1.17 (d, J=6.34 Hz, 3H), 1.23 (t, J=7.25 Hz, 3H), 1.19-2.02 (m, 14H), 3.09 (ddd, J=13.70, 10.99, 5.66 Hz, 1H), 4.10 (q, J=7.10 Hz, 2H), 4.17-4.30 (m, 3H), 4.34 (dd, J=13.59, 7.25 Hz, 1H), 8.13 (s, 2H).

MS (ESI) m/z: 377[M+H]$^+$ (Analysis conditions) Supercritical fluid chromatography using CHIRALPAK™ IF-3 (3.0 mm×50 mm) by Daicel (mobile phase: $CO_2$:methanol (70:30), 40° C., flow rate: 1.2 mL/min, detection: UV (245 nm)).

(Analysis results) The retention time of the title compound was 1.02 minutes, the cis:trans ratio was >99:1, and the optical purity was >99% ee.

(3) Synthesis of (1R,3s,5S)-3-((2S,4S)-1-(5-fluoropyrimidin-2-yl)-2-methylpiperidin-4-yl)-8-azabicyclo[3.2.1]octane A mixture of ethyl (1R,3s,5S)-3-((2S,4S)-1-(5-fluoropyrimidin-2-yl)-2-methylpiperidin-4-yl)-8-azabicyclo[3.2.1]octane-8-carboxylate (34 mg, 0.09 mmol) and 48% hydrobromic acid (2.0 mL) was stirred for 1 hour at 100° C. Aqueous 5 N sodium hydroxide was added to the reaction mixture at 0° C. for neutralization. The mixture was extracted 3 times with dichloromethane, and the organic layer was dried over anhydrous magnesium sulfate and concentrated under reduced pressure to obtain the title compound (21.7 mg).

MS (ESI) m/z: 305[M+H]$^+$ (4) Synthesis of (R)-2-cyclopropyl-2-((1R,3S,5S)-3-(2S,4S)-1-(5-fluoropyrimidin-2-yl)-2-methylpiperidin-4-yl)-8-azabicyclo[3.2.1]octan-8-yl)acetamide A mixture of (1R,3s,5S)-3-((2S,4S)-1-(5-fluoropyrimidin-2-yl)-2-methylpiperidin-4-yl)-8-azabicyclo[3.2.1]octane (5.00 mg, 0.016 mmol), potassium carbonate (4.54 mg, 0.033 mmol), (S)-2-bromo-2-cyclopropyl acetamide (8.24 mg, 0.033 mmol) and acetonitrile (1.0 mL) was stirred at room temperature for 7 days. Potassium carbonate (4.54 mg, 0.033 mmol) and (S)-2-bromo-2-cyclopropyl acetamide (8.24 mg, 0.033 mmol) were added to the reaction mixture, which was further stirred at room temperature for 3 days. An aqueous ammonium chloride solution was added to the reaction mixture to suspend the reaction. The mixture was extracted with ethyl acetate and the organic layer was rinsed with water and concentrated under reduced pressure to obtain a crude product.

The obtained crude product was diluted with methanol and supplied onto a Waters PoraPak Rxn™ CX (6 cc (400 mg) cartridge). After rinsing the solid phase with methanol (6.0 mL), it was eluted with ammonia (2 N methanol solution, 6 mL). The eluate was concentrated under reduced pressure and the obtained residue was purified by thin-layer chromatography (NH, dichloromethane) to obtain the title compound (3.74 mg).

$^1$H-NMR (400 MHz, CDCl$_3$) δ (ppm): 0.25-0.36 (m, 1H), 0.39-0.51 (m, 1H), 0.51-0.59 (m, 1H), 0.59-0.70 (m, 1H), 0.70-0.84 (m, 11H), 1.18 (d, J=6.34 Hz, 3H), 1.21-1.55 (m, 9H), 1.61-1.95 (m, 5H), 2.04 (d, J=9.06 Hz, 1H), 3.10 (ddd, J=13.70, 10.99, 5.21 Hz, 114), 3.15-3.28 (m, 1H), 3.80-3.94 (m, 1H), 4.17-4.29 (m, 1H), 4.35 (dd, J=13.59, 7.25 Hz, 1H), 5.18 (brs, 1H), 6.94 (brs, 1H), 8.14 (s, 2H).

MS (ESI) m/z: 402[M+H]$^+$

Figure 3:
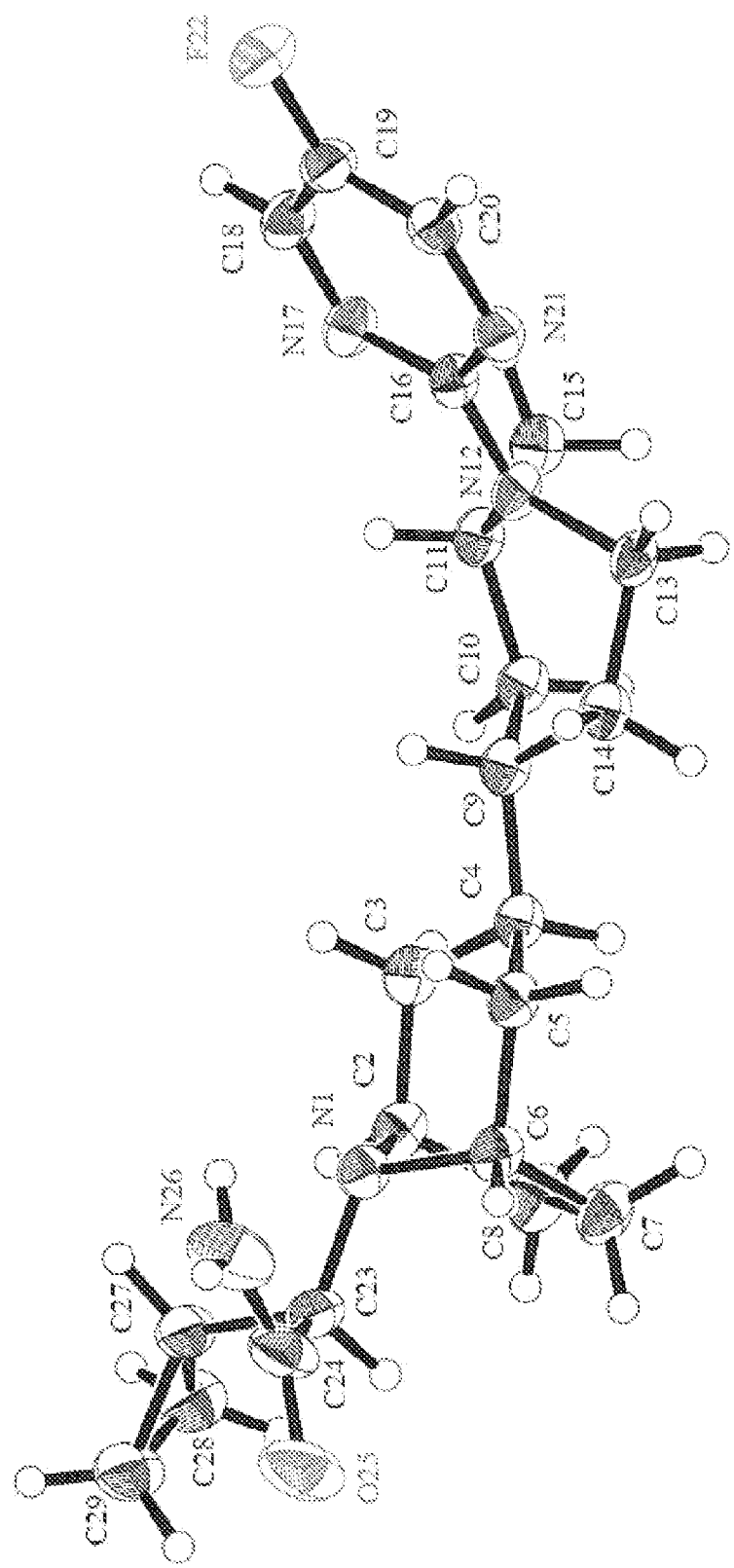
FIG. 3 is an ORTEP diagram showing the results of X-ray crystallographic analysis of the compound obtained in Example 4.

Preparation of (R)-2-cyclopropyl-2-((1R,3S,5S)-3-((2S,4S)-1-(5-fluoropyrimidin-2-yl)-2-methylpiperidin-4-yl)-8-azabicyclo[3.2.1]octan-8-yl)acetamide Single Crystal and X-Ray Crystallographic Analysis The title compound obtained in Example 4 (0.81 mg) was dissolved in methanol (600 μL). A vial containing a 200 μL portion thereof was gently placed in a slightly larger vial containing 2 mL of tert-butyl methyl ether, and the cap was closed (steam diffusion method). After 12 days, a single crystal of the title compound was obtained in the vial. The obtained single crystal was subjected to X-ray crystallographic analysis under the following conditions. The X-ray crystal structure of the title compound is shown in FIG. 3.

Analytical instrument: XtaLAB PRO P200 MM007HF (Rigaku, Japan)
Software: CrysAlisPro (Rigaku Oxford Diffraction)
X-rays: Multi-layer mirror monochromated Cu-Kα(40 kV/30 mA)
Measurement: ω axis oscillation method
Camera length: 35 mm
Measuring temperature: −170° C.

PHARMACOLOGICAL TEST EXAMPLES

The following pharmacological test was conducted using the compounds of Examples 1 to 4.

Test Example 1-1: Evaluation of Activity for OX1R and OX2R

HEK293 (human embryonic kidney 293) cells with forced expression of human OX1R (hOX1R) or human OX2R (hOX2R) were seeded in a 384-well microplate (Greiner) at 10,000 per well and cultured for 1 day in high-glucose-DMEM (FujiFilm Corp.—Wako Pure Chemical Industries, Ltd.) containing added 10% FBS (Tenno Scientific) and 1% Penicillin-Streptomycin (FujiFilm Corp.—Wako Pure Chemical Industries, Ltd.). After removing the medium, 40

μL of assay buffer (20 mM HEPES (Sigma-Aldrich Japan, KK.), Hanks' balanced salt solution (Gibco), 0.1% BSA (Sigma-Aldrich Japan, KK.), 0.1% Pluronic F-127 (Invitrogen)) containing Calcium 4 dye (Molecular Device Corporation) and 2.5 mM probenecid (Sigma-Aldrich Japan, KK.) were added, and the plate was incubated for 60 minutes. After further adding 20 μL of assay buffer, 20 μL of assay buffer containing the test compound was added and reaction was initiated. Change in intracellular calcium ion concentration during the reaction was measured based on the fluorescence intensity ratio in terms of the fluorescence value with wavelength excitation at 480 nm and detection at 540 nm, using FDSS7000 (Hamamatsu Photonics, K.K.). The test compound was dissolved in DMSO to 10 mM, and diluted with assay buffer to a final concentration of from $3\times10^{-11}$ M to $1\times10^{-7}$ M (DMSO final concentration of 0.1%). The half maximal effective concentration ($EC_{50}$ value) was determined from the fluorescence value with addition of the test compound at different concentrations, with the fluorescence value of the well with compound-free buffer added as 0%, and the fluorescence value of the well with 10 nM OX-A (Peptide Research Lab) as 100%. The $EC_{50}$ value of each compound is shown in Table 1.

TABLE 1

| Example No. | hOX1R $EC_{50}$ (nM) | hOX2R $EC_{50}$ (nM) |
| --- | --- | --- |
| 1 | >100 | 0.99 |
| 2 | >100 | 3.08 |

Test Example 1-2: Evaluation of Activating Activity for OX1R and OX2R

Human Embryonic Kidney cells 293 (HEK293) cells with forced expression of hOX1R or hOX2R were seeded in a 384-well microplate (Greiner) at 10,000 per well and cultured for 1 day in high-glucose-DMEM (FujiFilm Corp.—Wako Pure Chemical Industries, Ltd.) containing added 10% FBS (Thermo Scientific) and 1% Penicillin-Streptomycin (FujiFilm Corp.—Wako Pure Chemical Industries, Ltd.). After removing the medium, 30 μL of assay buffer (20 mM HEPES (Sigma-Aldrich Japan, KK.), Hank's balanced salt solution (Gibco), 0.1% BSA (Sigma-Aldrich Japan, KK.), 0.1% Pluronic F-127 (Invitrogen)) containing Calcium 4 dye (Molecular Device Corporation) and 2.5 mM probenecid (Sigma-Aldrich Japan, KK.) were added, and the mixture was incubated for 60 minutes. A 30 μL portion of assay buffer containing the test compound was added and reaction was initiated. Change in intracellular calcium ion concentration by the reaction was measured based on the fluorescence intensity ratio in terms of the fluorescence value with dual wavelength excitation at 480 nm and 540 nm, using FDSS7000 (Hamamatsu Photonics, K.K.). The test compound was dissolved in DMSO to 10 mM, and diluted with assay buffer to a final concentration of from $3\times10^{-11}$ M to $1\times10^{-5}$ M (DMSO final concentration of 0.1%). The $EC_{50}$ value was determined from the fluorescence value with addition of the test compound at different concentrations, with the fluorescence value of the well with compound-free buffer added as 0%, and the fluorescence value of the well with 30 nM OX-A (Peptide Research Lab) as 100%. The $EC_{50}$ value of each compound is shown in Table 2.

TABLE 2

| Example No. | hOX1R $EC_{50}$ (nM) | hOX2R $EC_{50}$ (nM) |
| --- | --- | --- |
| 1 | 4700 | 2.3 |
| 3 | 1400 | 4.3 |
| 4 | 3900 | 4.4 |

Test Example 2: Increase in Spontaneous Movement

Similar to increase in body temperature or increase in cardiovascular parameters such as blood pressure, increased movement in mice is one of indicator for wakefulness. In this test example, the alertness effect was evaluated by measuring spontaneous movement of the mice. Male C57BL/6NCrl mice (18-19 weeks old, Charles River Laboratories, Japan Inc., 4 mice in each group) were used for the experiment. Spontaneous movement was measured by using a movement measuring device (VersaMax Oven Field, AccuScan Instruments, Inc.), irradiating infrared rays from the side sections of the measuring cage, and quantifying the number of times that the mice passed through the irradiation. After placing the mice in the measuring cage and conditioning for 3 hours, the compound was orally administered (10 mg/kg). Spontaneous movement was measured 2 hours after administration. The test compound-administered group was administered a solution of the test compound dissolved in 0.1 moL/L hydrochloric acid containing 5% (v/v) DMSO and 5% (v/v) Kolliphor™ EL. For the control group, solvent alone without the test compound was administered to the mice.

The results are shown in Table 3. Spontaneous movement was represented as a percentage for the test compound-administered group, with spontaneous movement in the control group as 100%.

TABLE 3

| Test compound | Spontaneous movement (% of Control) |
| --- | --- |
| Solvent | 100 |
| Example 1 | 865 |
| Example 2 | 253 |

As shown in Table 3, the compounds of the invention augmented spontaneous movement in the mice. In other words, the compounds of the invention were shown to have an alertness effect.

Test Example 3: The Wake-Promoting Effect by Oral Administration of Invention Compound to Wild Type Mice The experimental animals used were C57BL/6 line wild type (WT) male mice. Electroencephalogram and electromyogram measuring electrodes were surgically embedded into 13-week-old mice under isoflurane anesthesia. The solvent (0 mg/kg) or a solution of the compound of Example 1 dissolved in the solvent (1, 3 or 10 mg/kg) was orally administered 30 to 15 minutes before lighting was turned off. The solvent used was a 0.1 moL/L hydrochloric acid solution containing 5% (v/v) DMSO and 5% (v/v) Kolliphor™ EL. The electroencephalogram and electromyogram were recorded for about 24 hours, from 1 hour before lighting was turned off. The mice were repeatedly used, with a washout period of 2 days or longer. The electroencephalogram and electromyogram data obtained for each mouse were used to assess the sleep stage every epoch (10 seconds), using sleep analysis software (SleepSign: Kissei Comtec Co., Ltd.). The time (sleep onset latency) until initial sleep was exhibited after lighting out (sleeping for 8 or more epochs beginning after non-REM sleep) was measured for each mouse. Using 16 mice in each administered group, the sleep onset latency in a solvent-administered group (control group) and an Example 1 compound-administered group were compared by a Dunnet-type multiple comparison test following survival time analysis in consideration of the number of experiments and use of the same individuals, with a significance level of 5% at both ends for each.

The sleep latencies of the mice administered the solvent and the Example 1 compound at 1, 3 and 10 mg/kg were 0.23 hour, 0.28 hour, 0.44 hour and 2.07 hours, respectively. In the Example 1 compound-administered groups with 3 or 10 mg/kg, the sleep onset latency increased significantly with respect to the solvent-administered group. Specifically, when the Example 1 compound was orally administered, sleep onset latency was found to be lengthened in a dost dependent manner.

Test Example 4: The Wake-Promoting Effect and Cataplexy-Free State Elongation by Oral Administration of Invention Compound to Orexin-Deficient Mice (Orexin/Ataxin-3 Tg/+ Mice)

The experimental animals used were orexin/ataxin-3 Tg/+ mice (hereunder referred to as "Tg mice", Ham et al., Neuron, 30,345-54,2001) with a C57BL/6 genetic background. Electroencephalogram and electromyogram measuring electrodes were surgically embedded into 12-week-old mice (±2 weeks) under isoflurane anesthesia. The solvent (0 mg/kg) or a solution of a sample (compound of Example 1 dissolved in the solvent: 0.3, 1 or 3 mg/kg) was orally administered 30 to 15 minutes before lighting was turned off. The solvent used was a 0.1 moL/L hydrochloric acid solution containing 5% (v/v) DMSO and 5% (v/v) Kolliphor™ EL. The electroencephalogram and electromyogram were recorded for about 24 hours, from 1 hour before lighting was turned off. The mice were repeatedly used, with a washout period of 2 days or longer. The electroencephalogram and electromyogram data obtained for each mouse were used to assess the sleep stage every epoch (10 seconds), using sleep analysis software (SleepSign: Kissei Comtec Co., Ltd.), up to a maximum of 4 hours (cut-off value). For the purpose of this experiment, cataplexy-like symptoms were defined as REM sleep appearing immediately after wakefulness (direct transition from wake to REM sleep (DREM)) for a contiguous period of 4 epochs or longer. DREM in mice is an analog of cataplexy (Exp Neurol. 2009; 217:46-54). The time until initial sleep appeared after lighting out for each mouse (sleep for contiguous 8 epochs or longer, excluding DREM)(sleep onset latency) and the time until initial DREM appeared (DREM latency) were measured. The numbers of mice were 14 in the vehicle group and Example 1 compound-administered groups. The sleep onset latency and DREM latency in a vehicle control group and a compound-administered group were compared by a Dunnet-type multiple comparison test following survival time analysis in consideration of the number of experiments and use of the same individuals, with a significance level of 5% at both ends for each.

The sleep onset latencies for Tg mice administered the solvent and the Example 1 compound at 0.3, 1 and 3 mg/kg were 0.21 hour, 0.31 hour, 0.64 hour and 2.42 hours, respectively, indicating significant increase in sleep onset latency in the Example 1 compound-administered groups with 1 and 3 mg/kg. Specifically, when the Example 1 compound was orally administered, sleep onset latency was found to be lengthened in a dose-dependent manner from 1 mg/kg in the orexin-deficient mice.

The DREM latencies with administration of solvent and administration of the Example 1 compound at 0.3, 1 and 3 mg/kg in the Tg mice were 1.16 hours, 1.50 hours, 2.26 hours and 4.00 hours, respectively, confirming that DREM latency was increased significantly and in a dose-dependent manner in the Example 1 compound-administered groups at 0.3, 1 and 3 mg/kg, compared to the solvent-administered group. In other words, murine cataplexy-like behavior-free states were extended by administration of the invention compounds in a dose-dependent manner.

What is claimed is:

1. A compound selected from the group consisting of (2R)-2-cyclopropyl-2-{(1R,3S,5S)-3-[(3S,4R)-1-(5-fluoropyrimidin-2-yl)-3-methoxypiperidin-4-yl]-8-azabicyclo [3.2.1]octan-8-yl}acetamide represented by the following formula (I):

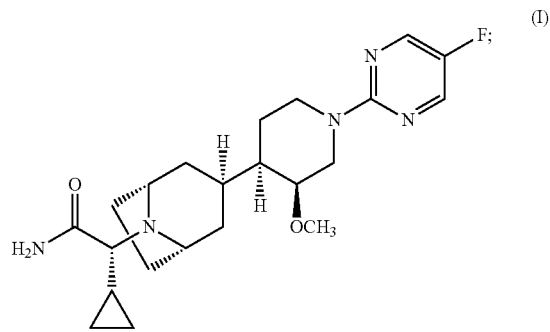 [SMILES: CO[C@@H]1CN(c2ncc(F)cn2)CC[C@@H]1[C@@H]1C[C@H]2CC[C@@H](C1)N2[C@@H](C(N)=O)C1CC1]

(R)-2-((1R,3S,5S)-3-((3S,4R)-1-(5-fluoropyrimidin-2-yl)-3-methoxypiperidin-4-yl)-8-azabicyclo[3.2.1]octan-8-yl)-3-methylbutaneamide represented by the following formula (II):

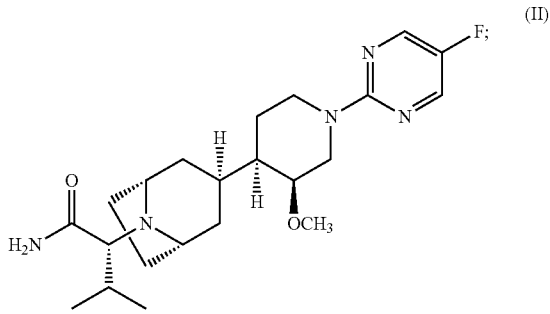 [SMILES: CO[C@@H]1CN(c2ncc(F)cn2)CC[C@@H]1[C@@H]1C[C@H]2CC[C@@H](C1)N2[C@@H](C(N)=O)C(C)C]

(R)-2-((1R,3S,5S)-3-((3S,4R)-1-(5-chloropyrimidin-2-yl)-3-ethoxypiperidin-4-yl)-8-azabicyclo[3.2.1]octan-8-yl)-2-cyclopropyl acetamide represented by the following formula (III):

(III)

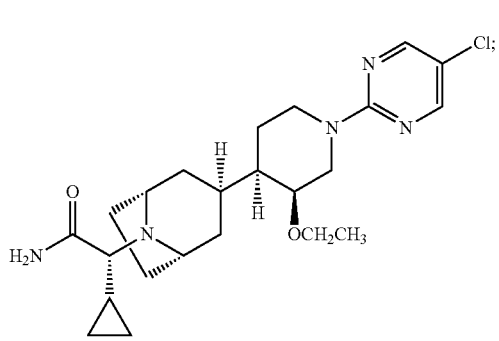

and (R)-2-cyclopropyl-2-((1R,3S,5S)-3-((2S, 4S)-1-(5-fluoropyrimidin-2-yl)-2-methylpiperidin-4-yl)-8-azabicyclo[3.2.1]octan-8-yl)acetamide represented by the following formula (IV):

(IV)

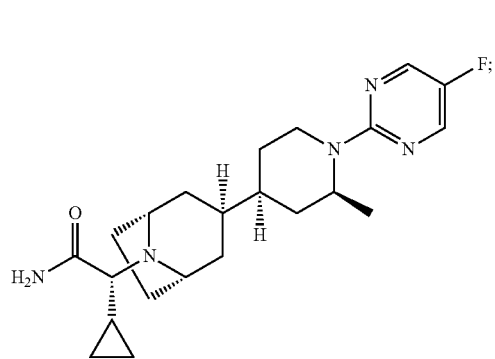

or a pharmaceutically acceptable salt thereof.

2. (2R)-2-Cyclopropyl-2-{(1R,3S,5S)-3-[(3S,4R)-1-(5-fluoropyrimidin-2-yl)-3-methoxypiperidin-4-yl]-8-azabicyclo[3.2.1]octan-8-yl}acetamide represented by the following formula (I):

(I)

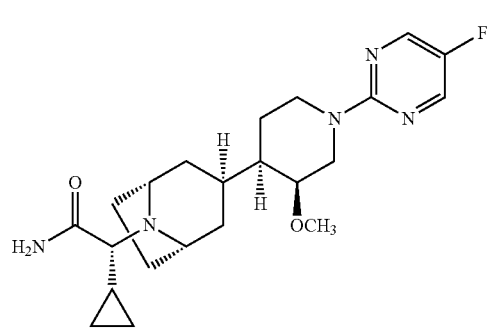

or a pharmaceutically acceptable salt thereof.

3. (R)-2-((1R,3S,5S)-3-((3S,4R)-1-(5-Fluoropyrimidin-2-yl)-3-methoxypiperidin-4-yl)-8-azabicyclo[3.2.1]octan-8-yl)-3-methylbutaneamide represented by the following formula (II):

(II)

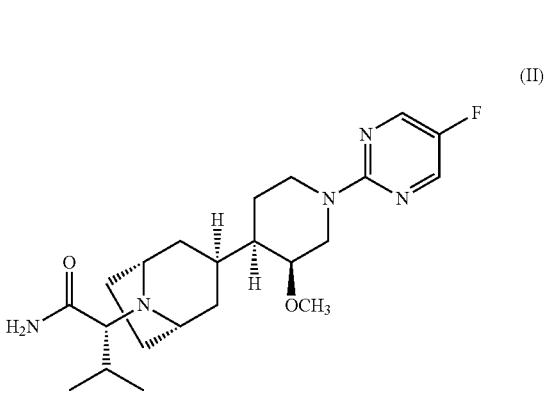 [SMILES: CO[C@@H]1CN(c2ncc(F)cn2)CC[C@@H]1[C@@H]1C[C@H]2CC[C@@H](C1)N2[C@@H](C(N)=O)C(C)C]

or a pharmaceutically acceptable salt thereof.

4. (R)-2-((1R,3S,5S)-3-((3S,4R)-1-(5-Chloropyrimidin-2-yl)-3-ethoxypiperidin-4-yl)-8-azabicyclo[3.2.1]octan-8-yl)-2-cyclopropyl acetamide represented by the following formula (III):

(III)

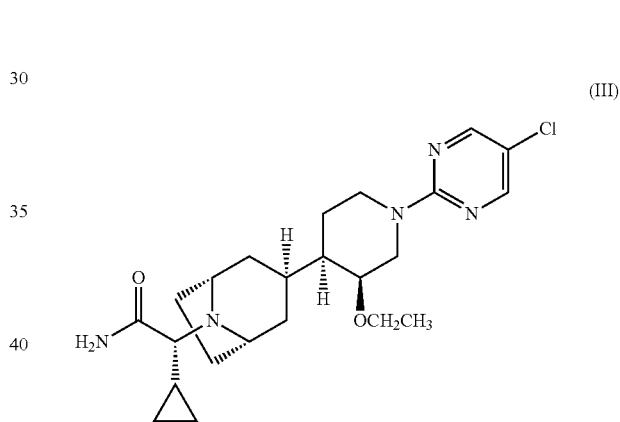

or a pharmaceutically acceptable salt thereof.

5. (R)-2-Cyclopropyl-2-((1R,3S,5S)-3-((2S, 4S)-1-(5-fluoropyrimidin-2-yl)-2-methylpiperidin-4-yl)-8-azabicyclo[3.2.1]octan-8-yl)acetamide represented by the following formula (IV):

(IV)

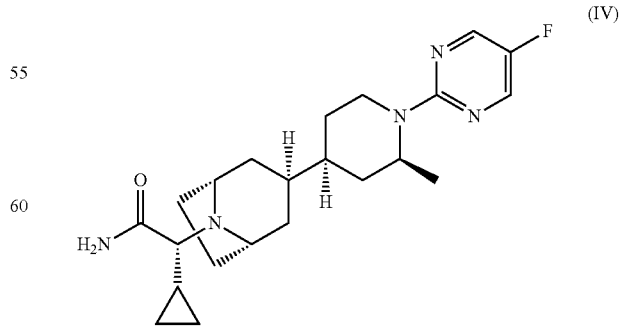

or a pharmaceutically acceptable salt thereof.

6. A pharmaceutical composition comprising the compound or a pharmaceutically acceptable salt thereof according to claim 1 and one or more pharmaceutically acceptable excipients.

7. A method of activating orexin type 2 receptor, comprising administering to a subject a pharmacologically effective dose of the compound or a pharmaceutically acceptable salt thereof according to claim 1.

8. A method of treating narcolepsy, comprising administering to a subject a pharmacologically effective dose of the compound or a pharmaceutically acceptable salt thereof according to claim 1.

9. A method of treating cataplexy, comprising administering to a subject a pharmacologically effective dose of the compound or a pharmaceutically acceptable salt thereof according to claim 1.

* * * * *

UNITED STATES PATENT AND TRADEMARK OFFICE
CERTIFICATE OF CORRECTION

| | |
|---|---|
| PATENT NO. | : 11,479,552 B2 |
| APPLICATION NO. | : 17/376452 |
| DATED | : October 25, 2022 |
| INVENTOR(S) | : Yu Yoshida et al. |

It is certified that error appears in the above-identified patent and that said Letters Patent is hereby corrected as shown below:

On the Title Page

On Page 2 Column 1, Item (56) (other Publications) Line 25 Delete "Pairkinson's" and insert -- Parkinson's --.

On Page 2 Column 1, Item (56) (other Publications) Line 29 Delete "Regulatoiy" and insert -- Regulatory --.

In the Specification

In Column 3 Line 3 Delete "methylbutaneamide" and insert -- methylbutanamide --.

In Column 4 Line 24 Delete "methylbutaneamide" and insert -- methylbutanamide --.

In Column 6 Line 39 Delete "thereof" and insert -- thereof, --.

In Column 7 Line 9 Delete "term"pharmaceutically" and insert -- term "pharmaceutically --.

In Column 7 Line 28 Delete "(II)" and insert -- (III) --.

In Column 7 Line 55 Delete "(I11)" and insert -- (III) --.

In Column 8 Line 31 Delete "lumiferin" and insert -- luciferin --.

In Column 9 Line 6 Delete "d" and insert -- d: --.

In Column 9 Line 15 Delete "(Silicagel)" and insert -- (Silica gel) --.

In Column 9 Line 17 Delete "3 L" and insert -- 3L --.

Signed and Sealed this
Twentieth Day of June, 2023

Katherine Kelly Vidal
*Director of the United States Patent and Trademark Office*

CERTIFICATE OF CORRECTION (continued)
U.S. Pat. No. 11,479,552 B2

In Column 9 Line 20 Delete "Prep100q" and insert -- Prep 100q --.

In Column 9 Line 54 Delete "128-08-5)(7.04" and insert -- 128-08-5) (7.04 --.

In Column 9 Line 59 Delete "mmol)" and insert -- mol) --.

In Column 10 Line 39 Delete "methylbutaneamide" and insert -- methylbutanamide --.

In Column 10 Line 50-51 Delete "dimethylfomamide" and insert -- dimethylformamide --.

In Column 10 Line 53 Delete "8)(9.80" and insert -- 8) (9.80 --.

In Column 12 Line 22 Delete "185099-67-6)(1.00" and insert -- 185099-67-6) (1.00 --.

In Column 13 Line 39 Delete "11H)," and insert -- 1H), --.

In Column 13 Line 55 Delete "ethylacetate." and insert -- ethyl acetate. --.

In Column 14 Line 2 Delete "10-60%/ethyl" and insert -- 10-60% ethyl --.

In Column 14 Line 11 Delete "-(3S,4R)-" and insert -- -((3S,4R)- --.

In Column 14 Line 13 Delete "carbaoxylate" and insert -- carboxylate --.

In Column 14 Line 36 Delete "3-(3S," and insert -- 3-((3S, --.

In Column 14 Line 50 Delete "tide" and insert -- title --.

In Column 15 Line 18 Delete "(2-cyclopropylacetyl-4" and insert -- (2-cyclopropylacetyl)-4 --.

In Column 18 Line 5 Delete "tide" and insert -- title --.

In Column 18 Line 25 Delete "methylbutaneamide" and insert -- methylbutanamide --.

In Column 19 Line 2 Delete "un," and insert -- run, --.

In Column 20 Line 22 Delete "mL)mixture" and insert -- mL) mixture --.

In Column 20 Line 22 Delete "tert-butyl(1R,3s,5S)-" and insert -- tert-butyl (1R,3s,5S)- --.

In Column 20 Line 38 Delete "ten-" and insert -- tert- --.

In Column 21 Line 22 Delete "(20:80),40° C.," and insert -- (20:80), 40° C., --.

In Column 21 Line 57 Delete "ng," and insert -- mg, --.

CERTIFICATE OF CORRECTION (continued)
U.S. Pat. No. 11,479,552 B2

In Column 22 Line 4 Delete "10%/ethyl" and insert -- 10% ethyl --.

In Column 22 Line 11 Delete "(s, 2H).MS" and insert -- (s, 2H). MS --.

In Column 22 Line 13 Delete "-3 (3S," and insert -- -3-((3S, --.

In Column 22 Line 29 Delete "ng)." and insert -- mg). --.

In Column 22 Line 56 Delete "tide" and insert -- title --.

In Column 25 Line 13 Delete "(silicagel," and insert -- (silica gel, --.

In Column 25 Line 29 Delete "un," and insert -- run, --.

In Column 26 Line 22 Delete "11H)," and insert -- 1H), --.

In Column 26 Line 24 Delete "114)," and insert -- 1H), --.

In Column 26 Line 65 Delete "(Tenno" and insert -- (Thermo --.

In Column 29 Line 11 Delete "Dunnet-type" and insert -- Dunnett-type --.

In Column 29 Line 23 Delete "dost" and insert -- dose --.

In Column 29 Line 33 Delete "Ham" and insert -- Hara --.

In Column 29 Line 34 Delete "30,345-54,2001)" and insert -- 30, 345-54, 2001) --.

In Column 29 Line 58 Delete "DREM)(sleep" and insert -- DREM) (sleep --.

In Column 29 Line 64 Delete "Dunnet-type" and insert -- Dunnett-type --.

In the Claims

In Column 30 Line 47 in Claim 1, delete "methylbutaneamide" and insert -- methylbutanamide --.

In Column 32 Line 3 in Claim 3, delete "methylbutaneamide" and insert -- methylbutanamide --.